US011603519B2

(12) United States Patent
Nakatsura et al.

(10) Patent No.: US 11,603,519 B2
(45) Date of Patent: Mar. 14, 2023

(54) T-CELL RECEPTOR

(71) Applicants: National Cancer Center Japan, Tokyo (JP); Kyoto University, Kyoto (JP); Takeda Pharmaceutical Company Limited, Osaka (JP)

(72) Inventors: Tetsuya Nakatsura, Chiba (JP); Toshiaki Yoshikawa, Chiba (JP); Yasushi Uemura, Chiba (JP); Kyoko Fukuda, Chiba (JP); Shin Kaneko, Kyoto (JP); Atsutaka Minagawa, Kyoto (JP); Yoshiaki Kassai, Kanagawa (JP); Atsushi Matsuda, Cambridge, MA (US)

(73) Assignees: National Cancer Center Japan, Tokyo (JP); Kyoto University, Kyoto (JP); Takeda Pharmaceutical Company Limited, Osaka (JP)

(*) Notice: Subject to any disclaimer, the term of this patent is extended or adjusted under 35 U.S.C. 154(b) by 696 days.

(21) Appl. No.: 16/483,876

(22) PCT Filed: Feb. 5, 2018

(86) PCT No.: PCT/JP2018/003799
§ 371 (c)(1),
(2) Date: Aug. 6, 2019

(87) PCT Pub. No.: WO2018/143454
PCT Pub. Date: Aug. 9, 2018

(65) Prior Publication Data
US 2020/0010804 A1 Jan. 9, 2020

(30) Foreign Application Priority Data

Feb. 6, 2017 (JP) .............. JP2017-019883

(51) Int. Cl.
*C12N 5/0783* (2010.01)
*A61P 35/00* (2006.01)
(Continued)

(52) U.S. Cl.
CPC ............ *C12N 5/0638* (2013.01); *A61K 35/17* (2013.01); *A61P 35/00* (2018.01);
(Continued)

(58) Field of Classification Search
None
See application file for complete search history.

(56) References Cited

U.S. PATENT DOCUMENTS 9,228,007 B1 * 1/2016 Kitchen ............... C12N 5/0636
2016/0083449 A1 * 3/2016 Schmitt ............. A61K 38/2013
435/235.1

FOREIGN PATENT DOCUMENTS

EP 2944652 A1 11/2015
WO 2004018667 A1 3/2004
(Continued)

OTHER PUBLICATIONS

Giegerich G, Pette M, Meinl E, Epplen JT, Wekerle H, Hinkkanen A. Diversity of T cell receptor α and β chain genes expressed by human T cells specific for similar myelin basic protein peptide/major histocompatibility complexes. European journal of immunology. Mar. 1992;22(3):753-8. (Year: 1992).*
(Continued)

*Primary Examiner* — Kevin K Hill
*Assistant Examiner* — Anjeanette Roberts
(74) *Attorney, Agent, or Firm* — McCarter & English, LLP; David G. Conlin; Andrew R. Ehle

(57) ABSTRACT

Provided is a T cell receptor capable of binding to a peptide having the amino acid sequence shown in SEQ ID NO: 27 or a complex of the peptide and HLA-A24. A T cell receptor
(Continued)

capable of binding to a peptide having the amino acid sequence shown in SEQ ID NO: 28 or a complex of the peptide and HLA-A02. Disclosed T cell receptors are useful in treating or avoiding cancers which are associated with expression of glypican-3.

17 Claims, 6 Drawing Sheets

Specification includes a Sequence Listing.

(51) Int. Cl.
    *A61K 35/17*       (2015.01)
    *C07K 14/725*     (2006.01)
    *C12N 15/86*      (2006.01)

(52) U.S. Cl.
    CPC .......... *C07K 14/7051* (2013.01); *C12N 15/86* (2013.01); *C12N 2506/45* (2013.01)

(56) References Cited

FOREIGN PATENT DOCUMENTS

| | | | | |
|---|---|---|---|---|
| WO | 2007018199 A1 | 2/2007 | | |
| WO | WO-2013057586 A1 * | 4/2013 | ......... | C07K 14/7051 |
| WO | 2013070468 A1 | 5/2013 | | |
| WO | 2015173112 A1 | 11/2015 | | |
| WO | WO-2015188119 A1 * | 12/2015 | ......... | A61K 31/4745 |
| WO | 2016010148 A1 | 1/2016 | | |
| WO | 2016092787 A1 | 6/2016 | | |
| WO | WO-2017158116 A1 * | 9/2017 | ............. | A61K 35/17 |
| WO | WO-2018067618 A1 * | 4/2018 | ............. | A61K 35/17 |

OTHER PUBLICATIONS

Tissot AC, Pecorari F, Plückthun A. Characterizing the functionality of recombinant T-cell receptors in vitro: a pMHC tetramer based approach. Journal of immunological methods. Mar. 6, 2000;236(1-2):147-65. (Year: 2000).*
Enokida T, Moreira A, Bhardwaj N. Vaccines for immunoprevention of cancer. The Journal of Clinical Investigation. May 3, 2021;131 (9) (Year: 2021).*
Fisher MA, Vinson JE, Gittleman JL, Drake JM. The description and number of undiscovered mammal species. Ecology and evolution. Apr. 2018;8(7):3628-35 (Year: 2018).*
Drexler M. The cancer miracle isn't a cure. It's prevention. Boston: Harvard Public Health. 2019, pp. 1-27. (Year: 2019).*
Kunert A, Straetemans T, Govers C, Lamers C, Mathijssen R, Sleijfer S, Debets R. TCR-engineered T cells meet new challenges to treat solid tumors: choice of antigen, T cell fitness, and sensitization of tumor milieu. Frontiers in Immunology. Nov. 8, 2013;4:363. (Year: 2013).*
Yoshikawa T, Nakatsugawa M, Suzuki S, Shirakawa H, et al. HLA-A2-restricted glypican-3 peptide-specific CTL clones induced by peptide vaccine show high avidity and antigen-specific killing activity against tumor cells. Cancer Science. May 2011;102(5):918-25. (Year: 2011).*
Gao H, Li K, Tu H, Pan X, Jiang H, Shi B, Kong J, Wang H, Yang S, Gu J, Li Z. Development of T cells redirected to glypican-3 for the treatment of hepatocellular carcinoma. Clin Cancer Res. 2014; 20:6418-6428. (Year: 2014).*
Li K, Pan X, Bi Y, Xu W, Chen C, Gao H, Shi B, Jiang H, Yang S, Jiang L, Li Z. Adoptive immunotherapy using T lymphocytes redirected to glypican-3 for the treatment of lung squamous cell carcinoma. Oncotarget. Jan. 19, 2016;7(3):2496. (Year: 2016).*
Chen C, Shi L, Li Y, Wang X, Yang S. Disease-specific dynamic biomarkers selected by integrating inflammatory mediators with clinical informatics in ARDS patients with severe pneumonia. Cell Biology and Toxicology. Jun. 2016;32(3):169-84. (Year: 2016).*
Perrin S. Preclinical research: Make mouse studies work. Nature. Mar. 2014;507(7493):423-5. (Year: 2014).*
Perro M, Tsang J, Xue SA, Escors D, Cesco-Gaspere M, Pospori C, Gao L, Hart D, Collins M, Stauss H, Morris EC. Generation of multi-functional antigen-specific human T-cells by lentiviral TCR gene transfer. Gene therapy. Jun. 2010;17(6):721-32. (Year: 2010).*
Lei F. Development of a T cell based cancer immunotherapy by using the induced pluripotent stem cell. Dissertation; 2013 (Year: 2013).*
Giegerich G, Pette M, Meinl E, Epplen JT, Wekerle H, Hinkkanen A. Diversity of T cell receptor a and 3 chain genes expressed by human T cells specific for similar myelin basic protein peptide/ major histocompatibility complexes. European journal of immunology. Mar. 1992;22(3):753-8. (Year: 1992).*
Dargel, C. et al. "T Cells Engineered to Express a T-Cell Receptor Specific for Glypican-3 to Recognize and Kill Hepatoma Cells in Vitro and in Mice", Gastroenterology, 149:1042-1052 (2015).
Supplementary Partial European Search Report corresponding to Application No. EP 18748529.7 dated Nov. 16, 2020.
English Translation of ISR corresponding to PCT Application PCT/JP2018/003799.
Database Geneseq [Online], Jan. 12, 2017 (Jan. 12, 2017), "Glypican-3 cytotoxicity T cell epitope peptide (298-306)", XP002801999, retrieved from EBI accession No. GSP: BDJ57973, Database accession No. BDJ57973.
Database Geneseq [Online], Jul. 28, 2016 (Jul. 28, 2016), "GPC3 protein CTL epitope (residues 144-152)", XP002802000, retrieved from EBI accession No. GSP: BCR52010, Database accession No. BCR52010.
Supplementary European Search Report corresponding to European Patent Application No. 18748529.7 dated Feb. 23, 2021.
Shimizu et al., Cancer immunotherapy-targeted glypican-3 or neoantigens. Cancer Sci. Mar. 2018;109(3):531-541.
Tsuchiya et al., Immunological efficacy of glypican-3 peptide vaccine in patients with advanced hepatocellular carcinoma. Oncoimmunology. Jul. 11, 2017;6(10):e1346764, 11 pages.
Yoshikawa et al., HLA-A2-restricted glypican-3 peptide-specific CTL clones induced by peptide vaccine show high avidity and antigen-specific killing activity against tumor cells. Cancer Sci. May 2011;102(5):918-25.
Yoshikawa et al., Proof of glypican-3 (GPC3) peptide specific CTLs infiltrating into tumor tissue derived from advanced HCC patient vaccinated with CPC3 peptide. AACR Special Conference Tumor Immunology. 1 page, Dec. 2-5, 2012.
International Preliminary Report on Patentability for Application No. PCT/JP2018/003799, dated Aug. 15, 2019, 7 pages.

* cited by examiner

A

CTL2-1

SK-Hep-1
/hGPC3

SK-Hep-1
/vec

B

CTL1-1  CTL1-2

SK-Hep-1
/hGPC3

SK-Hep-1
/vec

A TCR1-1'

B TCR2-1'

SEQUENCE LISTING

```
<160> NUMBER OF SEQ ID NOS: 56

<210> SEQ ID NO 1
<211> LENGTH: 6
<212> TYPE: PRT
<213> ORGANISM: Homo sapiens

<400> SEQUENCE: 1

Asp Ser Ser Ser Thr Tyr
1               5
```

```
<210> SEQ ID NO 2
<211> LENGTH: 7
<212> TYPE: PRT
<213> ORGANISM: Homo sapiens

<400> SEQUENCE: 2

Ile Phe Ser Asn Met Asp Met
1               5

<210> SEQ ID NO 3
<211> LENGTH: 13
<212> TYPE: PRT
<213> ORGANISM: Homo sapiens

<400> SEQUENCE: 3

Cys Ala Glu Arg Arg Ser Ser Ala Ser Lys Ile Ile Phe
1               5                   10

<210> SEQ ID NO 4
<211> LENGTH: 5
<212> TYPE: PRT
<213> ORGANISM: Homo sapiens

<400> SEQUENCE: 4

Ser Val Phe Ser Ser
1               5

<210> SEQ ID NO 5
<211> LENGTH: 7
<212> TYPE: PRT
<213> ORGANISM: Homo sapiens

<400> SEQUENCE: 5

Val Val Thr Gly Gly Glu Val
1               5

<210> SEQ ID NO 6
<211> LENGTH: 13
<212> TYPE: PRT
<213> ORGANISM: Homo sapiens

<400> SEQUENCE: 6

Cys Ala Gly Arg Tyr Ser Ser Ala Ser Lys Ile Ile Phe
1               5                   10

<210> SEQ ID NO 7
<211> LENGTH: 5
<212> TYPE: PRT
<213> ORGANISM: Homo sapiens

<400> SEQUENCE: 7

Ser Gly His Arg Ser
1               5

<210> SEQ ID NO 8
<211> LENGTH: 6
<212> TYPE: PRT
<213> ORGANISM: Homo sapiens

<400> SEQUENCE: 8

Tyr Phe Ser Glu Thr Gln
1               5

<210> SEQ ID NO 9
```

```
<211> LENGTH: 16
<212> TYPE: PRT
<213> ORGANISM: Homo sapiens

<400> SEQUENCE: 9

Cys Ala Ser Gln Gln Ser Ser Gly Val Ala Ile His Glu Gln Tyr Phe
1               5                   10                  15

<210> SEQ ID NO 10
<211> LENGTH: 5
<212> TYPE: PRT
<213> ORGANISM: Homo sapiens

<400> SEQUENCE: 10

Ser Gly Asp Leu Ser
1               5

<210> SEQ ID NO 11
<211> LENGTH: 6
<212> TYPE: PRT
<213> ORGANISM: Homo sapiens

<400> SEQUENCE: 11

Tyr Tyr Asn Gly Glu Glu
1               5

<210> SEQ ID NO 12
<211> LENGTH: 15
<212> TYPE: PRT
<213> ORGANISM: Homo sapiens

<400> SEQUENCE: 12

Cys Ala Ser Ser Val Gly Gly Gly Ala Pro Asn Glu Gln Phe Phe
1               5                   10                  15

<210> SEQ ID NO 13
<211> LENGTH: 6
<212> TYPE: PRT
<213> ORGANISM: Homo sapiens

<400> SEQUENCE: 13

Ala Thr Gly Tyr Pro Ser
1               5

<210> SEQ ID NO 14
<211> LENGTH: 7
<212> TYPE: PRT
<213> ORGANISM: Homo sapiens

<400> SEQUENCE: 14

Ala Thr Lys Ala Asp Asp Lys
1               5

<210> SEQ ID NO 15
<211> LENGTH: 15
<212> TYPE: PRT
<213> ORGANISM: Homo sapiens

<400> SEQUENCE: 15

Cys Ala Leu Asn Gln Ile Gly Thr Ser Tyr Gly Lys Leu Thr Phe
1               5                   10                  15

<210> SEQ ID NO 16
<211> LENGTH: 5
<212> TYPE: PRT
```

```
<213> ORGANISM: Homo sapiens

<400> SEQUENCE: 16

Ser Gly Asp Leu Ser
1               5

<210> SEQ ID NO 17
<211> LENGTH: 6
<212> TYPE: PRT
<213> ORGANISM: Homo sapiens

<400> SEQUENCE: 17

Tyr Tyr Asn Gly Glu Glu
1               5

<210> SEQ ID NO 18
<211> LENGTH: 14
<212> TYPE: PRT
<213> ORGANISM: Homo sapiens

<400> SEQUENCE: 18

Cys Ala Ser Ser Pro Trp Ser Glu Pro Tyr Glu Gln Tyr Phe
1               5                   10

<210> SEQ ID NO 19
<211> LENGTH: 132
<212> TYPE: PRT
<213> ORGANISM: Homo sapiens

<400> SEQUENCE: 19

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Arg Arg Ser Ser Ala Ser Lys Ile Ile Phe Gly Ser Gly Thr Arg Leu
        115                 120                 125

Ser Ile Arg Pro
    130

<210> SEQ ID NO 20
<211> LENGTH: 129
<212> TYPE: PRT
<213> ORGANISM: Homo sapiens

<400> SEQUENCE: 20

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
```

-continued

```
                 35                  40                  45
Ser Leu Gln Trp Tyr Arg Gln Glu Pro Gly Glu Gly Pro Val Leu Leu
 50                  55                  60

Val Thr Val Val Thr Gly Gly Glu Val Lys Lys Leu Lys Arg Leu Thr
 65                  70                  75                  80

Phe Gln Phe Gly Asp Ala Arg Lys Asp Ser Leu His Ile Thr Ala
                 85                  90                  95

Ala Gln Pro Gly Asp Thr Gly Leu Tyr Leu Cys Ala Gly Arg Tyr Ser
                100                 105                 110

Ser Ala Ser Lys Ile Ile Phe Gly Ser Gly Thr Arg Leu Ser Ile Arg
                115                 120                 125

Pro

<210> SEQ ID NO 21
<211> LENGTH: 134
<212> TYPE: PRT
<213> ORGANISM: Homo sapiens

<400> SEQUENCE: 21

Met Gly Ser Arg Leu Leu Cys Trp Val Leu Leu Cys Leu Leu Gly Ala
  1               5                  10                  15

Gly Pro Val Lys Ala Gly Val Thr Gln Thr Pro Arg Tyr Leu Ile Lys
                 20                  25                  30

Thr Arg Gly Gln Gln Val Thr Leu Ser Cys Ser Pro Ile Ser Gly His
                 35                  40                  45

Arg Ser Val Ser Trp Tyr Gln Gln Thr Pro Gly Gln Gly Leu Gln Phe
 50                  55                  60

Leu Phe Glu Tyr Phe Ser Glu Thr Gln Arg Asn Lys Gly Asn Phe Pro
 65                  70                  75                  80

Gly Arg Phe Ser Gly Arg Gln Phe Ser Asn Ser Arg Ser Glu Met Asn
                 85                  90                  95

Val Ser Thr Leu Glu Leu Gly Asp Ser Ala Leu Tyr Leu Cys Ala Ser
                100                 105                 110

Gln Gln Ser Ser Gly Val Ala Ile His Glu Gln Tyr Phe Gly Pro Gly
                115                 120                 125

Thr Arg Leu Thr Val Thr
            130

<210> SEQ ID NO 22
<211> LENGTH: 133
<212> TYPE: PRT
<213> ORGANISM: Homo sapiens

<400> SEQUENCE: 22

Met Gly Phe Arg Leu Leu Cys Cys Val Ala Phe Cys Leu Leu Gly Ala
  1               5                  10                  15

Gly Pro Val Asp Ser Gly Val Thr Gln Thr Pro Lys His Leu Ile Thr
                 20                  25                  30

Ala Thr Gly Gln Arg Val Thr Leu Arg Cys Ser Pro Arg Ser Gly Asp
                 35                  40                  45

Leu Ser Val Tyr Trp Tyr Gln Gln Ser Leu Asp Gln Gly Leu Gln Phe
 50                  55                  60

Leu Ile Gln Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                 85                  90                  95
```

```
Leu Ser Ser Leu Glu Leu Gly Asp Ser Ala Leu Tyr Phe Cys Ala Ser
            100                 105                 110

Ser Val Gly Gly Ala Pro Asn Glu Gln Phe Phe Gly Pro Gly Thr
            115                 120                 125

Arg Leu Thr Val Leu
        130

<210> SEQ ID NO 23
<211> LENGTH: 133
<212> TYPE: PRT
<213> ORGANISM: Homo sapiens

<400> SEQUENCE: 23

Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Asn
            100                 105                 110

Gln Ile Gly Thr Ser Tyr Gly Lys Leu Thr Phe Gly Gln Gly Thr Ile
        115                 120                 125

Leu Thr Val His Pro
        130

<210> SEQ ID NO 24
<211> LENGTH: 132
<212> TYPE: PRT
<213> ORGANISM: Homo sapiens

<400> SEQUENCE: 24

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Pro Trp Ser Glu Pro Tyr Glu Gln Tyr Phe Gly Pro Gly Thr Arg
            115                 120                 125

Leu Thr Val Thr
        130
```

<210> SEQ ID NO 25
<211> LENGTH: 141
<212> TYPE: PRT
<213> ORGANISM: Homo sapiens

<400> SEQUENCE: 25

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 26
<211> LENGTH: 179
<212> TYPE: PRT
<213> ORGANISM: Homo sapiens

<400> SEQUENCE: 26

```
Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 27
<211> LENGTH: 9
<212> TYPE: PRT
<213> ORGANISM: Homo sapiens

<400> SEQUENCE: 27

Glu Tyr Ile Leu Ser Leu Glu Glu Leu
1               5

<210> SEQ ID NO 28
<211> LENGTH: 9
<212> TYPE: PRT
<213> ORGANISM: Homo sapiens

<400> SEQUENCE: 28

Phe Val Gly Glu Phe Phe Thr Asp Val
1               5

<210> SEQ ID NO 29
<211> LENGTH: 273
<212> TYPE: PRT
<213> ORGANISM: Homo sapiens

<400> SEQUENCE: 29

Met Lys Thr Phe Ala Gly Phe Ser Phe Leu Phe Leu Trp Leu Gln Leu
1               5                   10                  15

Asp Cys Met Ser Arg Gly Glu Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Arg Arg Ser Ser Ala Ser Lys Ile Ile Phe Gly Ser Gly Thr Arg Leu
        115                 120                 125

Ser Ile Arg Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser

Ser

<210> SEQ ID NO 30
<211> LENGTH: 270
<212> TYPE: PRT
<213> ORGANISM: Homo sapiens

<400> SEQUENCE: 30

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Arg Tyr Ser
            100                 105                 110

Ser Ala Ser Lys Ile Ile Phe Gly Ser Gly Thr Arg Leu Ser Ile Arg
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 31
<211> LENGTH: 313
<212> TYPE: PRT
<213> ORGANISM: Homo sapiens

<400> SEQUENCE: 31

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

```
Arg Ser Val Ser Trp Tyr Gln Gln Thr Pro Gly Gln Gly Leu Gln Phe
 50                  55                  60

Leu Phe Glu Tyr Phe Ser Glu Thr Gln Arg Asn Lys Gly Asn Phe Pro
 65                  70                  75                  80

Gly Arg Phe Ser Gly Arg Gln Phe Ser Asn Ser Arg Ser Glu Met Asn
                 85                  90                  95

Val Ser Thr Leu Glu Leu Gly Asp Ser Ala Leu Tyr Leu Cys Ala Ser
                100                 105                 110

Gln Gln Ser Ser Gly Val Ala Ile His Glu Gln Tyr Phe Gly Pro Gly
                115                 120                 125

Thr Arg Leu Thr Val Thr Glu Asp Leu Lys Asn Val Phe Pro Pro Glu
                130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
                195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
                260                 265                 270

Gln Gln Gly Val Leu Ser Ala Thr Ile Leu Tyr Glu Ile Leu Leu Gly
                275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 32
<211> LENGTH: 312
<212> TYPE: PRT
<213> ORGANISM: Homo sapiens

<400> SEQUENCE: 32

Met Gly Phe Arg Leu Leu Cys Cys Val Ala Phe Cys Leu Leu Gly Ala
1               5                  10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
 50                  55                  60

Leu Ile Gln Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                 85                  90                  95

Leu Ser Ser Leu Glu Leu Gly Asp Ser Ala Leu Tyr Phe Cys Ala Ser
```

```
                100             105             110
Ser Val Gly Gly Ala Pro Asn Glu Gln Phe Phe Gly Pro Gly Thr
            115                 120             125
Arg Leu Thr Val Leu Glu Asp Leu Lys Asn Val Phe Pro Pro Glu Val
130                 135                 140
Ala Val Phe Glu Pro Ser Glu Ala Glu Ile Ser His Thr Gln Lys Ala
145                 150                 155                 160
Thr Leu Val Cys Leu Ala Thr Gly Phe Tyr Pro Asp His Val Glu Leu
                165                 170                 175
Ser Trp Trp Val Asn Gly Lys Glu Val His Ser Gly Val Ser Thr Asp
                180                 185                 190
Pro Gln Pro Leu Lys Glu Gln Pro Ala Leu Asn Asp Ser Arg Tyr Cys
                195                 200                 205
Leu Ser Ser Arg Leu Arg Val Ser Ala Thr Phe Trp Gln Asn Pro Arg
210                 215                 220
Asn His Phe Arg Cys Gln Val Gln Phe Tyr Gly Leu Ser Glu Asn Asp
225                 230                 235                 240
Glu Trp Thr Gln Asp Arg Ala Lys Pro Val Thr Gln Ile Val Ser Ala
                245                 250                 255
Glu Ala Trp Gly Arg Ala Asp Cys Gly Phe Thr Ser Glu Ser Tyr Gln
                260                 265                 270
Gln Gly Val Leu Ser Ala Thr Ile Leu Tyr Glu Ile Leu Leu Gly Lys
                275                 280                 285
Ala Thr Leu Tyr Ala Val Leu Val Ser Ala Leu Val Leu Met Ala Met
                290                 295                 300
Val Lys Arg Lys Asp Ser Arg Gly
305                 310

<210> SEQ ID NO 33
<211> LENGTH: 274
<212> TYPE: PRT
<213> ORGANISM: Homo sapiens

<400> SEQUENCE: 33

Met Asn Tyr Ser Pro Gly Leu Val Ser Leu Ile Leu Leu Leu Leu Gly
1               5                   10                  15
Arg Thr Arg Gly Asn Ser Val Thr Gln Met Glu Gly Pro Val Thr Leu
                20                  25                  30
Ser Glu Glu Ala Phe Leu Thr Ile Asn Cys Thr Tyr Thr Ala Thr Gly
            35                  40                  45
Tyr Pro Ser Leu Phe Trp Tyr Val Gln Tyr Pro Gly Glu Gly Leu Gln
        50                  55                  60
Leu Leu Leu Lys Ala Thr Lys Ala Asp Asp Lys Gly Ser Asn Lys Gly
65                  70                  75                  80
Phe Glu Ala Thr Tyr Arg Lys Glu Thr Thr Ser Phe His Leu Glu Lys
                85                  90                  95
Gly Ser Val Gln Val Ser Asp Ser Ala Val Tyr Phe Cys Ala Leu Asn
                100                 105                 110
Gln Ile Gly Thr Ser Tyr Gly Lys Leu Thr Phe Gly Gln Gly Thr Ile
                115                 120                 125
Leu Thr Val His Pro Asn Ile Gln Asn Pro Asp Pro Ala Val Tyr Gln
                130                 135                 140
Leu Arg Asp Ser Lys Ser Ser Asp Lys Ser Val Cys Leu Phe Thr Asp
145                 150                 155                 160
```

```
Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 34
<211> LENGTH: 311
<212> TYPE: PRT
<213> ORGANISM: Homo sapiens

<400> SEQUENCE: 34

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Pro Trp Ser Glu Pro Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255
```

```
Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 35
<211> LENGTH: 23
<212> TYPE: DNA
<213> ORGANISM: Artificial Sequence
<220> FEATURE:
<223> OTHER INFORMATION: forward primer for PCR amplification (TCR1-2
      alpha chain)

<400> SEQUENCE: 35
aagcactctt ctagcccaga gaa                                         23

<210> SEQ ID NO 36
<211> LENGTH: 20
<212> TYPE: DNA
<213> ORGANISM: Artificial Sequence
<220> FEATURE:
<223> OTHER INFORMATION: reverse primer for PCR amplification (TCR1-2
      alpha chain)

<400> SEQUENCE: 36
tagcagggcc tcgataatga                                             20

<210> SEQ ID NO 37
<211> LENGTH: 24
<212> TYPE: DNA
<213> ORGANISM: Artificial Sequence
<220> FEATURE:
<223> OTHER INFORMATION: forward primer for PCR amplification (TCR1-2
      beta chain)

<400> SEQUENCE: 37
agaatgctta ctacagagac acca                                        24

<210> SEQ ID NO 38
<211> LENGTH: 22
<212> TYPE: DNA
<213> ORGANISM: Artificial Sequence
<220> FEATURE:
<223> OTHER INFORMATION: reverse primer for PCR amplification (TCR1-2
      beta chain)

<400> SEQUENCE: 38
gtttagccta tttcgtactt gg                                          22

<210> SEQ ID NO 39
<211> LENGTH: 21
<212> TYPE: DNA
<213> ORGANISM: Artificial Sequence
<220> FEATURE:
<223> OTHER INFORMATION: forward primer for sequencing (TCR1-2 alpha
      chain)

<400> SEQUENCE: 39
acgccttcaa caacagcatt a                                           21

<210> SEQ ID NO 40
```

```
<211> LENGTH: 23
<212> TYPE: DNA
<213> ORGANISM: Artificial Sequence
<220> FEATURE:
<223> OTHER INFORMATION: reverse primer1 for sequencing (TCR1-2 alpha
      chain)

<400> SEQUENCE: 40
cagacttgtc actggattta gag                                              23

<210> SEQ ID NO 41
<211> LENGTH: 21
<212> TYPE: DNA
<213> ORGANISM: Artificial Sequence
<220> FEATURE:
<223> OTHER INFORMATION: reverse primer2 for sequencing (TCR1-2 alpha
      chain)

<400> SEQUENCE: 41
ggagcacagg ctgtcttaca a                                                21

<210> SEQ ID NO 42
<211> LENGTH: 21
<212> TYPE: DNA
<213> ORGANISM: Artificial Sequence
<220> FEATURE:
<223> OTHER INFORMATION: reverse primer3 for sequencing (TCR1-2 alpha
      chain)

<400> SEQUENCE: 42
atagcagggc ctcgataatg a                                                21

<210> SEQ ID NO 43
<211> LENGTH: 24
<212> TYPE: DNA
<213> ORGANISM: Artificial Sequence
<220> FEATURE:
<223> OTHER INFORMATION: forward primer1 for sequencing (TCR1-2 beta
      chain)

<400> SEQUENCE: 43
agaatgctta ctacagagac acca                                             24

<210> SEQ ID NO 44
<211> LENGTH: 21
<212> TYPE: DNA
<213> ORGANISM: Artificial Sequence
<220> FEATURE:
<223> OTHER INFORMATION: forward primer2 for sequencing (TCR1-2 beta
      chain)

<400> SEQUENCE: 44
gctgtgtttg agccatcaga a                                                21

<210> SEQ ID NO 45
<211> LENGTH: 23
<212> TYPE: DNA
<213> ORGANISM: Artificial Sequence
<220> FEATURE:
<223> OTHER INFORMATION: reverse primer1 for sequencing (TCR1-2 beta
      chain)

<400> SEQUENCE: 45
aggcagtatc tggagtcatt gag                                              23

<210> SEQ ID NO 46
<211> LENGTH: 22
```

-continued

```
<212> TYPE: DNA
<213> ORGANISM: Artificial Sequence
<220> FEATURE:
<223> OTHER INFORMATION: reverse primer2 for sequencing (TCR1-2 beta
      chain)

<400> SEQUENCE: 46
gtttagccta tttcgtactt gg                                              22

<210> SEQ ID NO 47
<211> LENGTH: 273
<212> TYPE: PRT
<213> ORGANISM: Homo sapiens

<400> SEQUENCE: 47

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Arg Arg Ser Ser Ala Ser Lys Ile Ile Phe Gly Ser Gly Thr Arg Leu
        115                 120                 125

Ser Ile Arg Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Cys Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 48
<211> LENGTH: 270
<212> TYPE: PRT
<213> ORGANISM: Homo sapiens

<400> SEQUENCE: 48
```

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
            35                  40                  45

Ser Leu Gln Trp Tyr Arg Gln Glu Pro Gly Glu Gly Pro Val Leu Leu
50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Arg Tyr Ser
            100                 105                 110

Ser Ala Ser Lys Ile Ile Phe Gly Ser Gly Thr Arg Leu Ser Ile Arg
            115                 120                 125

Pro Asn Ile Gln Asn Pro Asp Pro Ala Val Tyr Gln Leu Arg Asp Ser
            130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Cys Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 49
<211> LENGTH: 313
<212> TYPE: PRT
<213> ORGANISM: Homo sapiens

<400> SEQUENCE: 49

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
            35                  40                  45

Arg Ser Val Ser Trp Tyr Gln Gln Thr Pro Gly Gln Gly Leu Gln Phe
50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Gln Gln Ser Ser Gly Val Ala Ile His Glu Gln Tyr Phe Gly Pro Gly
            115                 120                 125

Thr Arg Leu Thr Val Thr Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 50
<211> LENGTH: 312
<212> TYPE: PRT
<213> ORGANISM: Homo sapiens

<400> SEQUENCE: 50

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Gly Gly Gly Ala Pro Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu 165                 170                 175
Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
            210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
            290                 295                 300

Val Lys Arg Lys Asp Ser Arg Gly
305                 310

<210> SEQ ID NO 51
<211> LENGTH: 274
<212> TYPE: PRT
<213> ORGANISM: Homo sapiens

<400> SEQUENCE: 51

Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Asn
            100                 105                 110

Gln Ile Gly Thr Ser Tyr Gly Lys Leu Thr Phe Gly Gln Gly Thr Ile
            115                 120                 125

Leu Thr Val His Pro Asn Ile Gln Asn Pro Asp Pro Ala Val Tyr Gln
            130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
            165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
            210                 215                 220

```
Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 52
<211> LENGTH: 311
<212> TYPE: PRT
<213> ORGANISM: Homo sapiens

<400> SEQUENCE: 52

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
        50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Pro Trp Ser Glu Pro Tyr Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly
305                 310
```

<210> SEQ ID NO 53
<211> LENGTH: 141
<212> TYPE: PRT
<213> ORGANISM: Homo sapiens

<400> SEQUENCE: 53

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 54
<211> LENGTH: 179
<212> TYPE: PRT
<213> ORGANISM: Homo sapiens

<400> SEQUENCE: 54

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

```
<210> SEQ ID NO 55
<211> LENGTH: 9
<212> TYPE: PRT
<213> ORGANISM: unknown
<220> FEATURE:
<223> OTHER INFORMATION: amino acid sequence of  of HIV.sub.19-27

<400> SEQUENCE: 55

Thr Leu Asn Ala Trp Val Lys Val Val
1               5

<210> SEQ ID NO 56
<211> LENGTH: 9
<212> TYPE: PRT
<213> ORGANISM: unknown
<220> FEATURE:
<223> OTHER INFORMATION: amino acid sequence of  of HIV.sub.583-591

<400> SEQUENCE: 56

Arg Tyr Leu Lys Asp Gln Gln Leu Leu
1               5
```

US 11,603,519 B2

T-CELL RECEPTOR

REFERENCE TO RELATED APPLICATION

This application is a 35 U.S.C. § 371 national stage filing of International Application No. PCT/JP2018/003799, filed Feb. 5, 2018, which in turn claims the benefit of priority to Japanese Patent Application 2017-019883, filed Feb. 6, 2017, the entire contents of each of which are expressly incorporated herein by reference.

SEQUENCE LISTING

The instant application contains a Sequence Listing which has been submitted electronically in ASCII format and is hereby incorporated by reference in its entirety. Said ASCII copy, created Dec. 30, 2021, is named 136021-00501_SL.txt and is 50,045 bytes in size.

TECHNICAL FIELD

The present invention relates to a novel T cell receptor specific for glypican-3.

BACKGROUND ART

Primary liver cancer is primarily hepatocellular carcinoma (HCC), and is the fifth most common cancer in our country. Its prognosis is very bad and the mortality rate is very high. One of the main causes of the poor prognosis is the limited treatment options for progressive HCC. For patients with progressive HCC, only symptomatic treatments such as local excision and administration of a multi-kinase inhibitor sorafenib are possible. Particularly in elderly people, the response rate of sorafenib is low and the incidence of side effects is high. Therefore, there is a demand for the development of a new treatment method that minimizes the risk of side effects and improves the survival rate of patients with progressive HCC.

Immunotherapy is considered to be one of the leading treatments for HCC. For example, glypican-3 (GPC 3) is particularly overexpressed in HCC and is also related to poor prognosis; it is therefore an ideal target for cancer immunotherapy against HCC. As an immunotherapeutic method against HCC, a treatment method using GPC3 specific antibody and human chimeric antigen receptor (CAR) targeting GPC3 has been reported (patent document 1). In addition, T cell receptor (TCR) specific for HLA-A02-restricted $GPC3_{367\text{-}375}$ peptide has also been reported (patent document 2).

TCR is a receptor used when T cells recognize antigens, and TCR is composed of dimers of α chain and β chain, or γ chain and δ chain. TCR forms a complex with the CD3 molecule group on the T cell surface, recognizes the antigen and transmits a stimulation signal to the T cell. Each TCR chain has a variable region and a constant region, the constant region has a short cytoplasmic portion penetrating the cell membrane, and the variable region is extracellularly present and binds to the antigen-HLA (MHC) complex. In the variable region, there are three regions called complementarity determining regions (CDRs), and these regions bind to the antigen-HLA (MHC) complex. The three CDRs are called CDR1, CDR2 and CDR3.

The present inventors established cytotoxic T cell (CTL) clones expressing various $GPC3_{14\text{-}152}$ peptide-specific TCRs from peripheral blood mononuclear cells (PBMCs) derived from patients vaccinated with HLA-A02 restricted $GPC3_{144\text{-}152}$ peptide (non-patent document 1). However, TCR sequence of these CTL clones is not disclosed in non-patent document 1.

DOCUMENT LIST

Patent Documents patent document 1: WO 2013/070468
patent document 2: WO 2015/173112

Non-Patent Document non-patent document 1: Yoshikawa T., et al., Cancer Sci 2011 (102): 918-925

SUMMARY OF THE INVENTION

Problems to be Solved by the Invention

The present invention aims to provide a novel T cell receptor (TCR) specifically recognizing glypican-3 (GPC3). In addition, the present invention aims to provide a medicament using the aforementioned TCR (e.g. using cytotoxic T cells comprising the TCR) for the prevention or treatment of cancer and tumor expressing GPC3.

Means of Solving the Problems

The present inventors established CTL clones from peripheral blood mononuclear cells (PBMCs) derived from patients vaccinated with GPC3 peptide (HLA-A24-restricted $GPC3_{298\text{-}306}$ peptide or HLA-A02-restricted $GPC3_{144\text{-}152}$ peptide) and decoded the TCR sequences of particular CTL clones. Based on the TCR sequences, they have conducted intensive studies and found that these TCRs are responsive to GPC3-expressing cancer cells, functional TCR can be efficiently expressed by gene transfection of a TCR with a specified modification in the constant region of TCR into cells, and the like, which resulted in the completion of the present invention.

That is, the present invention provides the following.
[1] A T cell receptor (TCR) comprising,
as complementarity determining regions of the α chain,
  the amino acid sequence shown in SEQ ID NO: 1,
  the amino acid sequence shown in SEQ ID NO: 2, and
  the amino acid sequence shown in SEQ ID NO: 3; or
  the amino acid sequence shown in SEQ ID NO: 4,
  the amino acid sequence shown in SEQ ID NO: 5, and
  the amino acid sequence shown in SEQ ID NO: 6, and
as complementarity determining regions of the β chain,
  the amino acid sequence shown in SEQ ID NO: 7,
  the amino acid sequence shown in SEQ ID NO: 8, and
  the amino acid sequence shown in SEQ ID NO: 9; or
  the amino acid sequence shown in SEQ ID NO: 10,
  the amino acid sequence shown in SEQ ID NO: 11, and
  the amino acid sequence shown in SEQ ID NO: 12,
wherein said TCR is capable of binding to a peptide having the amino acid sequence shown in SEQ ID NO: 27 or a complex of the peptide and HLA-A24.
[2] A T cell receptor (TCR) comprising,
as complementarity determining regions of the α chain,
  the amino acid sequence shown in SEQ ID NO: 13,
  the amino acid sequence shown in SEQ ID NO: 14, and
  the amino acid sequence shown in SEQ ID NO: 15; and
as complementarity determining regions of the β chain,
  the amino acid sequence shown in SEQ ID NO: 16,
  the amino acid sequence shown in SEQ ID NO: 17, and
  the amino acid sequence shown in SEQ ID NO: 18, wherein said TCR is capable of binding to a peptide having the amino acid sequence shown in SEQ ID NO: 28 or a complex of the peptide and HLA-A02.

[3] A T cell receptor (TCR) comprising, as an α chain variable region,
the amino acid sequence shown in SEQ ID NO: 19,
the amino acid sequence shown in SEQ ID NO: 19 wherein one or several amino acids are deleted, substituted or added, or
an amino acid sequence having 90% or more identity with the amino acid sequence shown in SEQ ID NO: 19; or
the amino acid sequence shown in SEQ ID NO: 20,
the amino acid sequence shown in SEQ ID NO: 20 wherein one or several amino acids are deleted, substituted or added, or
an amino acid sequence having 90% or more identity with the amino acid sequence shown in SEQ ID NO: 20, and
as a β chain variable region,
the amino acid sequence shown in SEQ ID NO: 21,
the amino acid sequence shown in SEQ ID NO: 21 wherein one or several amino acids are deleted, substituted or added, or
an amino acid sequence having 90% or more identity with the amino acid sequence shown in SEQ ID NO: 21; or
the amino acid sequence shown in SEQ ID NO: 22,
the amino acid sequence shown in SEQ ID NO: 22 wherein one or several amino acids are deleted, substituted or added, or
an amino acid sequence having 90% or more identity with the amino acid sequence shown in SEQ ID NO: 22,
wherein said TCR is capable of binding to a peptide having the amino acid sequence shown in SEQ ID NO: 27 or a complex of the peptide and HLA-A24.

[4] A T cell receptor (TCR) comprising as an α chain variable region,
the amino acid sequence shown in SEQ ID NO: 23,
the amino acid sequence shown in SEQ ID NO: 23 wherein one or several amino acids are deleted, substituted or added, or
an amino acid sequence having 90% or more identity with the amino acid sequence shown in SEQ ID NO: 23, and
as a β chain variable region,
the amino acid sequence shown in SEQ ID NO: 24,
the amino acid sequence shown in SEQ ID NO: 24 wherein one or several amino acids are deleted, substituted or added, or
an amino acid sequence having 90% or more identity with the amino acid sequence shown in SEQ ID NO: 24,
wherein said TCR is capable of binding to a peptide having the amino acid sequence shown in SEQ ID NO: 28 or a complex of the peptide and HLA-A02.

[5] The T cell receptor of any of [1] to [4], comprising as an α chain constant region,
the amino acid sequence shown in SEQ ID NO: 25,
the amino acid sequence shown in SEQ ID NO: 25 wherein one or several amino acids are deleted, substituted or added, or
an amino acid sequence having 90% or more identity with the amino acid sequence shown in SEQ ID NO: 25, and
as a β chain constant region,
the amino acid sequence shown in SEQ ID NO: 26,
the amino acid sequence shown in SEQ ID NO: 26 wherein one or several amino acids are deleted, substituted or added, or
an amino acid sequence having 90% or more identity with the amino acid sequence shown in SEQ ID NO: 26.

[6] A nucleic acid encoding the T cell receptor of any of [1] to [5].
[7] An expression vector comprising the nucleic acid of [6].
[8] A cell comprising the nucleic acid of [6] or the vector of [7].
[9] The cell of [8], wherein the cell is a lymphocyte or a pluripotent stem cell.
[10] The cell of [8], wherein the cell is a cytotoxic T lymphocyte.
[10-1] A cell comprising an exogenous nucleic acid that encodes the T cell receptor of any of [1] to [5].
[10-2] An induced pluripotent stem cell comprising an exogenous nucleic acid that encodes the T cell receptor of any of [1] to [5].
[10-3] A hematopoietic progenitor cell comprising an exogenous nucleic acid that encodes the T cell receptor of any of [1] to [5].
[10-4] A T cell comprising an exogenous nucleic acid that encodes the T cell receptor of any of [1] to [5].
[11] A method of producing the cell of [8], comprising a step of introducing the nucleic acid of [6] or the vector of [7] into the cell.
[12] A T cell induced from a pluripotent stem cell comprising the nucleic acid of [6] or the vector of [7].
[13] A method of producing a T cell, comprising the following steps:
(1) a step of differentiating a pluripotent stem cell comprising the nucleic acid of [6] or the vector of [7] into a hematopoietic progenitor cell, and
(2) a step of differentiating the hematopoietic progenitor cell into a T cell, and optionally
(3) a step of expanding the T cell.
[14] The method according to [13], wherein said T cell is a cytotoxic T cell, in particular a CD8 positive cytotoxic T cell.
[15] A medicament comprising the cell of any of [8] to [10] and [12].
[16] The medicament of [15] for use in the prevention or the treatment of cancer.
[17] A killing agent for a cell expressing glypican-3, comprising the cell of any of [8] to [10] and [12].
[18] A method of preventing or treating cancer in a mammal, comprising administering an effective amount of the cell of any of [8]-[10] and [12] to the mammal.
[19] The cell of any of [8] to [10] and [12] for use in the prevention or the treatment of cancer.
[20] Use of the cell of any of [8] to [10] and [12] in the manufacture of a preventive agent or therapeutic agent for cancer.

Effect of the Invention

The T cell receptor of the present invention has binding ability to GPC3 peptide (HLA-A24-restricted GPC3$_{298-306}$ peptide or HLA-A02-restricted GPC3$_{144-152}$ peptide) or a complex of the peptide and HLA-A molecule (HLA-A24 or HLA-A02). In addition, a nucleic acid encoding the aforementioned T cell receptor may impart cytotoxic activity against a cell presenting HLA-A molecule and GPC3 peptide to T cells, and therefore, it is useful for the prevention or the treatment of a cancer or a tumor expressing GPC3.

DESCRIPTION OF EMBODIMENTS

1. T Cell Receptor

Figure 1:
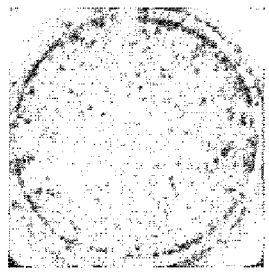
FIG. 1 shows the results of an ELISPOT assay on interferon-γ for the measurement of the antigen specific CTL response.
Figure 1:
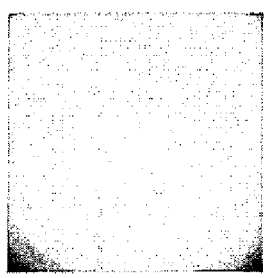
Figure 1:
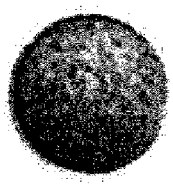
Figure 1:
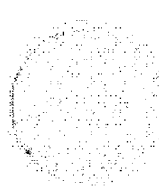

The present invention provides a T cell receptor (also called TCR) capable of binding to $GPC3_{298\text{-}306}$ peptide or a complex of the peptide and HLA-A24 (hereinafter to be abbreviated as "TCR1 of the present invention"). In addition, the present invention provides a T cell receptor capable of binding to $GPC3_{144\text{-}152}$ peptide or a complex of the peptide and HLA-A02 (hereinafter to be abbreviated as "TCR2 of the present invention"). In the following, "TCR1 of the present invention" and "TCR2 of the present invention" are sometimes abbreviated collectively as "TCR of the present invention". The TCR of the present invention may be isolated.

In the present invention, "T cell receptor (TCR)" means a receptor constituted of a dimer of TCR chains (α chain, β chain), recognizes the antigen or the antigen-HLA (human leukocyte antigen) (MHC; major histocompatibility complex) complex and transmits a stimulation signal to the T cells. Each TCR chain is constituted of a variable region and a constant region, and the variable region contains three complementarity determining regions (CDR1, CDR2, CDR3). The TCR of the present invention encompasses not only one in which the α chain and the β chain of the TCR constitute a heterodimer but also one in which they constitute a homodimer. Furthermore, the TCR of the present invention also encompasses one lacking a part of or whole constant region, one with recombination of an amino acid sequence, a soluble TCR and the like.

In the present invention, "soluble TCR" means a TCR solubilized by chemical modification of the TCR, binding to a Fc receptor, removal of transmembrane domain and the like, and being "soluble" means, for example, the property of permitting presence as a monodispersed heterodimer in phosphate buffered saline (PBS) (KCl 2.7 mM, $KH_2PO_4$ 1.5 mM, NaCl 137 mM and $Na_2PO_4$ 8 mM, pH 7.1-7.5), and means that not less than 90% of the TCR can remain as a monodispersed heterodimer after incubation at 25° C. for 1 hr. To increase stability of a soluble TCR, a new artificial disulfide bond may be introduced between the constant regions of each chain. Such soluble TCR can be produced, for example, according to the methods described in WO 2004/074322, Boulter et al., Clin Exp Immunol, 2005, 142(3): 454-460 and the like. When a soluble TCR is used, the concentration thereof is not particularly limited as long as the TCR can bind to an antigen or an antigen-HLA complex. For example, when a soluble TCR is used for an in vitro test, the concentration thereof is preferably 40 μg/ml or higher.

In the present invention, "$GPC3_{298\text{-}306}$ peptide" or "HLA-A24-restricted $GPC3_{29\text{-}306}$ peptide" means a peptide fragment of glypican-3(GPC3) consisting of the amino acid sequence shown in SEQ ID NO: 27. In a preferable embodiment, TCR1 of the present invention specifically recognizes and is capable of binding to a complex of $GPC3_{298\text{-}306}$ peptide and HLA-A24. Similarly, in the present invention, "$GPC3_{144\text{-}152}$ peptide" or "HLA-A02-restricted $GPC3_{144\text{-}152}$ peptide" means a peptide fragment of GPC3 consisting of the amino acid sequence shown in SEQ ID NO: 28 in the Sequence Listing. In a preferable embodiment, TCR2 of the present invention specifically recognizes and is capable of binding to a complex of $GPC3_{144\text{-}152}$ peptide and HLA-A02. In the following, "$GPC3_{298\text{-}306}$ peptide" and "$GPC3_{144\text{-}152}$ peptide" are sometimes abbreviated collectively as "GPC3 peptide".

It can be confirmed by a known method that the TCR of the present invention specifically recognizes and is capable of binding to the above-mentioned complex. A suitable method includes, for example, dextramer assay, ELISPOT assay etc. using HLA-A24 molecule or HLA-A02 molecule, and GPC3 peptide. By performing the ELISPOT assay, it can be confirmed that T cells expressing the TCR on the cell surface recognize the target cells by the TCR and the signal thereof has been transmitted into the cells.

The term "capable of binding" as used herein means "having an ability to bind" and refers to a capability to form a non-covalent complex with one or more other molecules. Examples of the complex according to the present invention include a complex of a GPC3 peptide and an HLA molecule (e.g. HLA-A24 or HLA-A02), and a complex of a GPC3 peptide and a TCR. Another example of a complex according to the present invention is a complex of a TCR and a GPC3 peptide which itself is in a complex with an HLA. Various methods and assays to determine binding capability are known in the art. Binding is usually a binding with high affinity, wherein the affinity as measured as a KD value is preferably less than 1 μM, more preferably less than 100 nM, even more preferably less than 10 nM, even more preferably less than 1 nM, even more preferably less than 100 μM, even more preferably less than 10 μM, even more preferably less than 1 μM. The term "KD" or "KD value" relates to the equilibrium dissociation constant as known in the art. In the context of the present invention, these terms can relate to the equilibrium dissociation constant of a TCR with respect to a particular antigen of interest (e.g. a peptide of GPC3 as defined herein or the respective complexes between the peptide and an HLA). The equilibrium dissociation constant is a measure of the propensity of a complex (e.g. a TCR-peptide-HLA complex) to reversibly dissociate into its components (e.g. the TCR and the peptide-HLA complex). Methods to determine a KD value are known in the art and are exemplified e.g. by the surface plasmon resonance.

In the present invention, being "isolated" means a state that a certain component (e.g. a TCR) is identified, separated or recovered from components of its natural environment.

In the present invention, "one or several amino acids" means e.g. 1, 2, 3, 4 or 5 amino acids, for example 1 to 4 amino acids, 1 to 3 amino acids or 1 to 2 amino acids. For example in the context of a TCR CDR region, one or several amino acids preferably means 1, 2 or 3 amino acids. In the context of a TCR variable region or a TCR, one or several amino acids preferably means 1 to 5, 1 to 4 or 1 to 3, in particular 1, 2 or 3 amino acids.

In the present invention, "% identity" means e.g. 90% or more (e.g., 91%, 92%, 93%, 94%, 95%, 96%, 97%, 98% or 99% or more) identity. An identity of an amino acid sequence can be calculated using homology calculation algorithm NCBI BLAST (National Center for Biotechnology Information Basic Local Alignment Search Tool) (blast.ncbi.nlm.nih.gov/Blast.cgi) and under the following conditions (expectancy=10; gap allowed; matrix=BLOSUM62; filtering=OFF). It is understood that for determining % identity a sequence of the present invention over its entire length is compared to another sequence. In other words, % identity according to the present invention excludes comparing a short fragment (e.g. 1 to 3 amino acids) of a sequence of the present invention to another sequence or vice versa.

In one embodiment of the present invention, the complementarity determining regions of the α chain of TCR1 of the present invention comprises the respective amino acid sequences of CDR1 to CDR3 shown in SEQ ID NOs: 1 to 3, respectively, or the amino acid sequences of CDR1 to CDR3 shown in SEQ ID NOs: 4 to 6, respectively, and the complementarity determining regions of the β chain of TCR1 comprises the respective amino acid sequences of CDR1 to CDR3 shown in SEQ ID NOs: 7 to 9, respectively, or the respective amino acid sequences of CDR1 to CDR3 shown in SEQ ID NOs: 10 to 12, respectively. In the above-mentioned amino acid sequences, 1 to several (e.g., 2, 3) amino acids may be deleted, substituted or added as long as a TCR comprising said amino acid sequences of CDR1 to CDR3 has an ability to bind to GPC3$_{298\text{-}306}$ peptide or a complex of the peptide and HLA-A24. In a preferable embodiment, TCR1 of the present invention comprises a TCR α chain comprising respective amino acid sequences of CDR1 to CDR3 shown in SEQ ID NOs: 1 to 3, respectively, and a TCR β chain comprising respective amino acid sequences of CDR1 to CDR3 shown in SEQ ID NOs: 7 to 9, respectively, and the α chain and the β chain of the TCR form a heterodimer. In another preferable embodiment, TCR1 of the present invention comprises a TCR α chain comprising respective amino acid sequences of CDR1 to CDR3 shown in SEQ ID NOs: 4 to 6, respectively, and a TCR β chain comprising respective amino acid sequences of CDR1 to CDR3 shown in SEQ ID NOs: 10 to 12, respectively, and the α chain and the β chain of the TCR form a heterodimer.

In another embodiment of the present invention, TCR1 of the present invention comprises a TCR α chain comprising CDR3 shown in SEQ ID NO: 6 and a TCR β chain comprising CDR3 shown in SEQ ID NO: 12, and the α chain and the β chain of the TCR form a heterodimer. Preferably this heterodimer has the capability of binding to GPC3$_{298\text{-}306}$ peptide or a complex of the peptide and HLA-A24.

In still another embodiment of the present invention, the complementarity determining regions of the α chain of TCR2 of the present invention comprises respective amino acid sequences of CDR 1 to CDR 3 shown in SEQ ID NOs: 13 to 15, respectively, and the complementarity determining regions of the β chain of TCR2 of the present invention comprises the respective amino acid sequences of CDR 1 to CDR 3 shown in SEQ ID NO: 16 to 18, respectively. In the above-mentioned amino acid sequences, 1 to several (e.g., 2, 3) amino acids may be deleted, substituted or added as long as a TCR comprising said amino acid sequences of CDR1 to CDR3 has an ability to bind to GPC3$_{144\text{-}152}$ peptide or a complex of the peptide and HLA-A02. In a preferable embodiment, TCR2 of the present invention comprises a TCR α chain comprising respective amino acid sequences of CDR1 to CDR3 shown in SEQ ID NOs: 13 to 15, respectively, and a TCR S chain comprising respective amino acid sequences of CDR1 to CDR3 shown in SEQ ID NOs: 16 to 18, respectively, and the α chain and the β chain of the TCR form a heterodimer.

In still another embodiment of the present invention, TCR2 of the present invention comprises a TCR α chain comprising CDR3 shown in SEQ ID NO: 15 and a TCR β chain comprising CDR3 shown in SEQ ID NO: 18, and the α chain and the β chain of the TCR form a heterodimer. Preferably, said heterodimer has the capability to bind to GPC3$_{144\text{-}152}$ peptide or a complex of the peptide and HLA-A02.

In still another embodiment of the present invention, the α chain of TCR1 of the present invention preferably includes a variable region of the α chain shown by the amino acid sequence shown in SEQ ID NO: 19, the amino acid sequence shown in SEQ ID NO: 19 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 19, with the proviso that the TCR comprising said variable region of the α chain is capable of binding to GPC3$_{298\text{-}306}$ peptide or a complex of the peptide and HLA-A24. Alternatively, the α chain of TCR1 of the present invention preferably includes a variable region of the α chain shown by the amino acid sequence shown in SEQ ID NO: 20, the amino acid sequence shown in SEQ ID NO: 20 in which one or several (e.g., 2, 3, 4, 5) amino acids are deleted, substituted or added, or an amino sequence having 90% or more (e.g., 91%, 92%, 93%, 94%, 95%, 96%, 97%, 98% or 99% or more) identity with the amino acid sequence shown in SEQ ID NO: 20, with the proviso that the TCR comprising said variable region of the α chain is capable of binding to GPC3$_{298\text{-}306}$ peptide or a complex of the peptide and HLA-A24. The variable region preferably contains respective amino acid sequences of CDR1 to CDR3 shown in SEQ ID NOs: 1 to 3, respectively, or respective amino acid sequences of CDR1 to CDR3 shown in SEQ ID NOs: 4 to 6, respectively. The identity of the amino acid sequence can be calculated as defined above. The identity of the following amino acid sequences can be calculated similarly.

In addition, the β chain of TCR1 of the present invention preferably includes a variable region of the β chain shown by the amino acid sequence shown in SEQ ID NO: 21, the amino acid sequence shown in SEQ ID NO: 21 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 21, with the proviso that the TCR comprising said variable region of the β chain is capable of binding to GPC3$_{298\text{-}306}$ peptide or a complex of the peptide and HLA-A24. Alternatively, the β chain of TCR1 of the present invention preferably includes a variable region of the β chain shown by the amino acid sequence shown in SEQ ID NO: 22, the amino acid sequence shown in SEQ ID NO: 22 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 22, with the proviso that the TCR comprising said variable region of the β chain is capable of binding to GPC3$_{298-306}$ peptide or a complex of the peptide and HLA-A24. The variable region preferably contains respective amino acid sequences of CDR1 to CDR3 shown in SEQ ID NOs: 7 to 9, respectively, or respective amino acid sequences of CDR1 to CDR3 shown in SEQ ID NOs: 10 to 12, respectively.

In a preferable embodiment, TCR1 of the present invention comprises a TCR α chain comprising the amino acid sequence shown in SEQ ID NO: 19, and a TCR β chain comprising the amino acid sequence shown in SEQ ID NO: 21, and the α chain and the β chain of the TCR form a heterodimer. In another preferable embodiment, TCR1 of the present invention comprises a TCR α chain comprising the amino acid sequence shown in SEQ ID NO: 20, and a TCR β chain comprising the amino acid sequence shown in SEQ ID NO: 22, and the α chain and the β chain of the TCR form a heterodimer.

In another embodiment of the present invention, the α chain of TCR2 of the present invention preferably includes a variable region of the α chain shown by the amino acid sequence shown in SEQ ID NO: 23, the amino acid sequence shown in SEQ ID NO: 23 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 23, with the proviso that the TCR comprising said variable region of the α chain is capable of binding to GPC3$_{144-152}$ peptide or a complex of the peptide and HLA-A02. The variable region preferably contains respective amino acid sequences of CDR1 to CDR3 shown in SEQ ID NOs: 13 to 15, respectively.

In addition, the β chain of TCR2 of the present invention preferably includes a variable region of the β chain shown by the amino acid sequence shown in SEQ ID NO: 24, the amino acid sequence shown in SEQ ID NO: 24 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 24, with the proviso that the TCR comprising said variable region of the β chain is capable of binding to GPC3$_{144-152}$ peptide or a complex of the peptide and HLA-A02. The variable region preferably contains respective amino acid sequences of CDR1 to CDR3 shown in SEQ ID NOs: 16 to 18, respectively.

In a preferable embodiment, TCR2 of the present invention comprises a TCR α chain comprising the amino acid sequence shown in SEQ ID NO: 23, and a TCR β chain comprising the amino acid sequence shown in SEQ ID NO: 24, and the α chain and the β chain of the TCR may form a heterodimer.

Furthermore, the α chain of TCR of the present invention preferably includes a constant region of the α chain shown by the amino acid sequence shown in SEQ ID NO: 25 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 25, with the proviso that the TCR comprising said constant region of the α chain is capable of transmitting a stimulation signal to a T cell. In a particular embodiment of the present invention, the constant region of the α chain includes the amino acid sequence shown in SEQ ID NO: 25. In addition, the β chain of the TCR of the present invention preferably includes a constant region of the β chain shown by the amino acid sequence shown in SEQ ID NO: 26 in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence shown in SEQ ID NO: 26, with the proviso that the TCR comprising said constant region of the β chain is capable of transmitting a stimulation signal to a T cell. In a particular embodiment of the present invention, the constant region of the β chain includes the amino acid sequence shown in SEQ ID NO: 26.

In addition, the constant region of the α chain or the β chain of the TCR of the present invention is preferably subjected to specified modification in the constant region of the α chain or the β chain of the TCR of the original CTL clone. Examples of this modification include, but are not limited to, enhancement of a dimer expression efficiency due to a disulfide bond between the α chain and the β chain by substituting a particular amino acid residue in the constant region of the TCR of the CTL clone with a cysteine residue (e.g., substitution of the 48th threonine in the constant region of the TCR α chain with cysteine (i.e., substitution of constant region of the TCR α chain with SEQ ID NO: 53), substitution of the 57th serine in the constant region of the TCR β chain of the CTL clone with cysteine (i.e., substitution of constant region of TCR β chain with SEQ ID NO: 54)).

Examples of the α chain of TCR1 of the present invention having the aforementioned variable region and constant region include, but are not limited to, a polypeptide consisting of the amino acid sequence shown in SEQ ID NO: 29, 30, 47 or 48 and the like. Examples of the β chain of TCR1 of the present invention having the aforementioned variable region and constant region include, but are not limited to, a polypeptide consisting of the amino acid sequence shown in SEQ ID NO: 31, 32, 49 or 50 and the like. Furthermore, the α chain or the β chain of the TCR, which is shown by either the amino acid sequence of said polypeptide in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence of said polypeptide can also be preferably used in the present invention, with the proviso that a TCR comprising said α chain or said β chain is capable of binding to GPC3$_{298-306}$ peptide or a complex of the peptide and HLA-A24. As TCR1 of the present invention, a heterodimer constituted of the α chain shown in SEQ ID NO: 29 and the β chain shown in SEQ ID NO: 31 (in the present specification, the above-mentioned heterodimer is sometimes referred to as TCR1-1), a heterodimer constituted of the α chain shown in SEQ ID NO: 47 and the β chain shown in SEQ ID NO: 49 (in the present specification, the above-mentioned heterodimer is sometimes referred to as TCR1-1'), a heterodimer constituted of the α chain shown in SEQ ID NO: 30 and the β chain shown in SEQ ID NO: 32 (in the present specification, the above-mentioned heterodimer is sometimes referred to as TCR1-2), or a heterodimer constituted of the α chain shown in SEQ ID NO: 48 and the β chain shown in SEQ ID NO: 50 (in the present specification, the above-mentioned heterodimer is sometimes referred to as TCR1-2') is preferable.

Examples of the α chain of TCR2 of the present invention having the aforementioned variable region and constant region include, but are not limited to, a polypeptide consisting of the amino acid sequence shown in SEQ ID NO: 33 or 51 and the like. Examples of the β chain of TCR2 of the present invention having the aforementioned variable region and constant region include, but are not limited to, a polypeptide consisting of the amino acid sequence shown in SEQ ID NO: 34 or 52 and the like. Furthermore, α chain or β chain of TCR, which is shown by either the amino acid sequence of said polypeptide in which one or several (e.g., 2, 3, 4, 5) amino acids are deleted, substituted or added, or an amino acid sequence having 90% or more (e.g., 91%, 92%, 93%, 94%, 95%, 96%, 97%, 98% or 99% or more) identity with the amino acid sequence of said polypeptide can also be preferably used in the present invention, with the proviso that preferably, a TCR comprising said α chain or said β chain is capable of binding to $GPC3_{144-152}$ peptide or a complex of the peptide and HLA-A02. As TCR2 of the present invention, a heterodimer constituted of the α chain shown in SEQ ID NO: 33 and the β chain shown in SEQ ID NO: 34 (in the present specification, the above-mentioned heterodimer is sometimes referred to as TCR2-1), or a heterodimer constituted of the α chain shown in SEQ ID NO: 51 and the β chain shown in SEQ ID NO: 52 (in the present specification, the above-mentioned heterodimer is sometimes referred to as TCR2-1') is preferable.

The TCR of the present invention can be genetically engineered using the nucleic acid or the vector of the present invention described later. For example, by introducing both a nucleic acid encoding the α chain of the TCR of the present invention and a nucleic acid encoding the β chain of the TCR of the present invention into a cell to express the α chain and the β chain polypeptide of the TCR, etc., the TCR of the present invention is expressed in the cell, and the cell can be isolated by a method known per se.

2. Nucleic Acid of the Present Invention

The present invention provides a nucleic acid encoding the aforementioned TCR of the present invention (hereinafter to be abbreviated as "the nucleic acid of the present invention"). The nucleic acid of the present invention may be isolated.

The nucleic acid of the present invention may be either a nucleic acid encoding the α chain of the TCR, a nucleic acid encoding the β chain of the TCR, or a nucleic acid encoding both α chain and β chain of the TCR.

The present invention also relates to nucleic acids encoding any one or more of the CDRs, the variable regions and/or the constant regions as described herein.

The present invention also encompasses a nucleic acid capable of hybridizing, under stringent conditions, to the complement of any of the nucleic acids defined herein. In a preferred embodiment, the nucleic acid capable of hybridizing encodes an amino acid sequence of a CDR, a variant region or a constant region having a function as described herein. Specifically, the nucleic acid capable of hybridizing encodes an amino acid sequence such that a TCR comprising said amino acid sequence has an ability to a) bind to $GPC3_{298-306}$ peptide or a complex of the peptide and HLA-A24; or b) bind to $GPC3_{144-152}$ peptide or a complex of the peptide and HLA-A02.

The nucleic acid encoding the α chain of TCR1 of the present invention may be any as long as it is a nucleic acid encoding the α chain of TCR1 defined above. For example, a nucleic acid encoding the polypeptide shown in SEQ ID NO: 29, 30, 47 or 48 and the like can be mentioned. In addition, the nucleic acid encoding the β chain of TCR1 of the present invention may be any as long as it is a nucleic acid encoding the β chain of TCR1 defined above. For example, a nucleic acid encoding the polypeptide shown in SEQ ID NO: 31, 32, 49 or 50 and the like can be mentioned.

The nucleic acid encoding the α chain of TCR2 of the present invention may be any as long as it is a nucleic acid encoding the α chain of TCR2 defined above. For example, a nucleic acid encoding the polypeptide shown in SEQ ID NO: 33 or 51 and the like can be mentioned. In addition, the nucleic acid encoding the β chain of TCR2 of the present invention may be any as long as it is a nucleic acid encoding the β chain of TCR2 defined above. For example, a nucleic acid encoding the polypeptide shown in SEQ ID NO: 34 or 52 and the like can be mentioned.

The nucleic acid of the present invention may be DNA or RNA, or DNA/RNA chimera, and preferably DNA. In addition, the nucleic acid may be double-stranded or single-stranded. In the case of double strands, a double-stranded DNA, a double-stranded RNA or a DNA:RNA hybrid may be used. When the nucleic acid is an RNA, T in the Sequence Listing is to be read as U as regards the RNA sequence. In addition, the nucleic acid of the present invention may contain a natural nucleotide, a modified nucleotide, a nucleotide analogue, or a mixture of these as long as it can express the polypeptide in vitro or in a cell.

The nucleic acid of the present invention can be constructed by a method known per se. For example, based on the amino acid sequence or the nucleic acid sequence of the TCR described in the Sequence Listing, a DNA strand is chemically synthesized, or synthesized partially overlapping oligo DNA short chains are connected using a PCR method or a Gibson Assembly method, whereby a DNA encoding the full length or a part of the TCR of the present invention can be constructed.

3. Expression Vector Containing the Nucleic Acid of the Present Invention

The nucleic acid of the present invention can be incorporated into an expression vector. Therefore, the present invention provides an expression vector containing any of the aforementioned nucleic acids of the present invention (hereinafter to be abbreviated as "the vector of the present invention").

The vector of the present invention may be a vector that does not integrate into the genome of a target cell. In one embodiment, the vector that does not integrate into the genome is capable of replicating outside the genome of the target cell. The vector may be present in multiple copies outside the genome of the target cell. In a further embodiment of the present invention, the vector integrates into the genome of the target cell. In a preferable embodiment, the vector integrates at a pre-defined location of the genome of the target cell.

Examples of the promoter to be used in the vector of the present invention include EF1α promoter, CAG promoter, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter, TCR V α gene promoter, TCR V β gene promoter and the like. Of these, EF1α promoter, CAG promoter, MoMuLV LTR, CMV promoter, SRα promoter and the like are preferable.

The vector of the present invention may contain a transcription and translation regulatory sequence, a ribosome binding site, an enhancer, a replication origin, a polyA addition signal, a selection marker gene and the like on demand besides the above-mentioned promoters. Examples of the selection marker gene include dihydrofolate reductase gene, neomycin resistance gene, puromycin resistance gene and the like.

In one embodiment of the present invention, heterodimers of a α chain and a β chain of the TCR can be constructed in a target cell or on the cell surface by introducing an expression vector containing a nucleic acid encoding the α chain and a nucleic acid encoding the β chain of the TCR of the present invention described above into the target cell. In this case, the nucleic acid encoding the α chain of the TCR and the nucleic acid encoding β chain of the TCR may be incorporated into separate expression vectors or a single expression vector. When they are incorporated into a single expression vector, these two kinds of nucleic acids are preferably incorporated via a sequence enabling polycistronic expression. Using a sequence enabling polycistronic expression, plural genes incorporated in one kind of expression vector can be more efficiently expressed. Examples of the sequence enabling polycistronic expression include T2A sequence of foot-and-mouth disease virus (PLoS ONE3, e2532, 2008, Stem Cells 25, 1707, 2007), internal ribosome entry site (IRES) (U.S. Pat. No. 4,937,190) and the like. From the aspect of uniform expression levels, T2A sequence is preferable.

The expression vector that can be used in the present invention is not particularly limited as long as it can express TCR for a sufficient period of time for preventing or treating a disease when introduced into a cell. Examples thereof include viral vector, plasmid vector and the like. As the virus vector, retrovirus vector (including lentivirus vector and pseudotype vector), adenovirus vector, adeno-associated virus vector, herpes virus vector, Sendaivirus, episomal vector and the like can be mentioned. A transposon expression system (PiggyBac system) may also be used. As the plasmid vector, animal cell expression plasmid (e.g., pa1-11, pXT1, pRc/CMV, pRc/RSV, pcDNAI/Neo) and the like can be mentioned.

4. Cell Comprising the Nucleic Acid or the Vector of the Present Invention

When the nucleic acid or the vector of the present invention is introduced into a cell and TCR1 is present on the cell surface, the cell may have an HLA-A24 restricted GPC3$_{298-306}$ specific cytotoxic activity against the target cell. Similarly, when the nucleic acid or the vector of the present invention is introduced into a cell and TCR2 of the present invention is present on the cell surface, the cell may have an HLA-A02 restricted GPC3$_{144-152}$ specific cytotoxic activity. Therefore, the present invention provides a cell comprising the nucleic acid or the vector of the present invention (in other words, a cell having the nucleic acid or the vector of the present invention) (hereinafter to be abbreviated as "the cell of the present invention"). Here, it is preferable that the nucleic acid of the present invention in the form of the vector of the present invention is introduced into a desired cell. The present invention also encompasses introducing the nucleic acid of the present invention into a host genome by genome editing (for example, CRISPR system, TALEN system). A preferable embodiment of the cell of the present invention includes, but is not limited to, a cell into which both a nucleic acid encoding the TCR α chain and a nucleic acid encoding the TCR β chain are introduced. Whether the cell of the present invention has a cytotoxic activity can be confirmed by a known method, and a preferable method includes, for example, measurement of a cytotoxic activity on HLA-A24 or HLA-A02 positive target cells such as chrome release assay and the like. In a preferable embodiment, the cell of the present invention is a human cell.

As a cell into which the nucleic acid or the expression vector of the present invention is introduced, for example, lymphocytes and progenitor cells of lymphocytes including pluripotent stem cells can be mentioned. In the present invention, the "lymphocyte" means one of the subtypes of leukocytes in the immune system of vertebrata. Examples of the lymphocyte include T cell, B cell, and natural killer cell (NK cell). Since a T cell receptor plays an important role in recognizing a T cell antigen, T cells are preferably cells into which the nucleic acid or the vector of the present invention is introduced. In the present invention, the "T cell" means one kind of leukocyte found in a lymphoid organ, peripheral blood and the like, and one classification of lymphocytes characterized by differentiation and maturation mainly in the thymus and expression of a T cell receptor (TCR). Examples of the T cell usable in the present invention include cytotoxic T lymphocyte (CTL) which is a CD8 positive cell, helper T cell which is a CD4 positive cell, regulatory T cell, effector T cell and the like, with preference given to the cytotoxic T lymphocyte. In addition, CD4/CD8 double positive cells are also encompassed in a T cell. T cells expressing the TCR of the present invention can be obtained by introducing the nucleic acid or the vector of the present invention into T cells collected from a living body. Alternatively, T cells expressing the TCR of the present invention (namely, T cells derived from the progenitor cells) can be obtained by inducing from lymphocyte progenitor cells (e.g., pluripotent stem cells) into which the nucleic acid or the vector of the present invention has been introduced.

The cell of the present invention (e.g., cytotoxic T cell) also has, in addition to the TCR gene inherently present in the cell, an exogenous TCR gene derived from the nucleic acid or the vector of the present invention. On this point, the cell of the present invention is different from the cells harvested from the living body.

The aforementioned lymphocytes can be collected from, for example, peripheral blood, bone marrow and cord blood of a human or a non-human mammal. When a cell transfected with the TCR gene of the present invention is used for the treatment of diseases such as cancer, the cell population is preferably collected from the subject to be treated or from a donor matched with the HLA type of the treatment target. Preferably, the subject or donor is a human.

Examples of the progenitor cell of lymphocytes include pluripotent cells, which include embryonic stem cell (ES cell), induced pluripotent stem cell (iPS cell), embryonic carcinoma cell (EC cell), embryonic germ cell (EG cell), hematopoietic stem cell, multipotent progenitor cell (MMP) without self-replication competence, myelo-lymphoid progenitor (MLP) cell, myeloid progenitor (MP) cell, granulomonocyte progenitor (GMP) cell, macrophage-dendritic cell progenitor (MDP) cell, dendritic cell precursor (DCP) cell and the like. Any cell derived from a human embryo and in particular an ES cell may be a cell produced by destroying the embryo or a cell prepared without destroying the embryo. From ethical point of view, iPS cell, EC cell, EG cell, hematopoietic progenitor cell, MMP, MLP, MP, GMP, MDP, DCP and ES cell prepared without destroying the embryo are preferable.

iPS cell is an artificial stem cell derived from a somatic cell having characteristics substantially equal to those of ES cell, for example, pluripotency and proliferation potency by self-replication, and can be produced by introducing particular reprogramming factors in the form of a DNA or a protein into a somatic cell (e.g., Takahashi K. and Yamanaka S. (2006) Cell, 126; 663-676: Takahashi K. et al. (2007) Cell, 131; 861-872: Yu J. et al. (2007) Science, 318; 1917-1920: Nakagawa M. et al. (2008) Nat. Biotechnol. 26; 101-106). When an iPS cell is used, it may be produced from a somatic cell by a method known per se or an iPS cell already established and stocked may also be used. While the somatic cell from which the iPS cell to be used in the present invention is derived is not limited, it is preferably a cell derived from peripheral blood or cord blood. The animal from which a pluripotent stem cell is derived is not limited and, for example, mammals such as mouse, rat, hamster, guinea pig, dog, monkey, orangutan, chimpanzee, human and the like can be mentioned, with preference given to human.

In the present invention, the "hematopoietic progenitor cell" means a CD34 positive cell, preferably, a CD34/CD43 double positive (DP) cell. The derivation of the hematopoietic progenitor cell to be used in the present invention is not particularly limited and may be obtained by, for example, inducing differentiation of a pluripotent stem cell by the method described below, or isolated from a biological tissue by a known method.

There is no particular limitation on the method for introducing the nucleic acid or the vector of the present invention into cells, and known methods can be used. When the nucleic acid or the plasmid vector is introduced, for example, a calcium phosphate coprecipitation method, a PEG method, an electroporation method, a microinjection method, a lipofection method and the like can be used. For example, the methods described in Cell Engineering additional volume 8, New Cell Engineering experiment protocol, 263-267 (1995) (published by Shujunsha), Virology, vol. 52, 456 (1973), Folia Pharmacol. Jpn., vol. 119 (No. 6), 345-351 (2002) and the like can be used. When a virus vector is used, the nucleic acid of the present invention is introduced into a suitable packaging cell (e.g., Plat-E cell) and a complementation cell line (e.g., 293 cell), the virus vector produced in the culture supernatant is recovered, and cells are infected with the vector by an appropriate method suitable for each virus vector, whereby the vector is introduced into the cells. For example, when a retrovirus vector is used as the vector, a specific means is disclosed in WO 2007/69666, Cell, 126, 663-676 (2006) and Cell, 131, 861-872 (2007) and the like. Particularly, when a retrovirus vector is used, highly efficient transfection into various cells is possible by using a recombinant fibronectin fragment CH-296 (manufactured by Takara Bio Inc.).

The nucleic acid of the present invention may also be directly introduced into cells in the form of an RNA and used to express a TCR in the cells. As a method for introducing the RNA, a known method can be used and, for example, a lipofection method, an electroporation method, or the like can be preferably used.

When the nucleic acid of the present invention is introduced into T cells, expression of the endogenous TCR α chain and the TCR β chain intrinsically expressed by the T cell may be suppressed by an siRNA in view of an increased expression of the TCR of the present invention, suppression of emergence of a mispaired TCR, and suppression of a non-self-reactivity. When the aforementioned nucleic acid is applied to this method, to avoid the effect of the siRNA on the TCR of the present invention, it is preferable that the nucleotide sequence of the nucleic acid encoding the TCR be a sequence (codon conversion type sequence) different from the nucleotide sequence corresponding to the RNA acted on by the siRNA suppressing the expression of the endogenous TCR α chain and the TCR β chain. These methods are described in, for example, WO 2008/153029. The aforementioned base sequence can be produced by introducing a silent mutation into a nucleic acid encoding a TCR obtained naturally or chemically synthesizing an artificially designed nucleic acid. To avoid mispairing with the endogenous TCR chain, a part or all of the constant regions of the nucleic acid encoding the TCR of the present invention may also be substituted with a constant region derived from an animal other than human, such as mouse.

5. Production Method of the Cell of the Present Invention

The present invention also provides a production method of the cell of the present invention, including a step of introducing the nucleic acid or the vector of the present invention into a cell (hereinafter to be abbreviated as "the production method of the present invention"). The cell into which the nucleic acid or the vector of the present invention is introduced, the introduction method and the like are as described in 4.

In one embodiment of the production method of the present invention, a production method of a T cell including (1) a step of differentiating pluripotent stem cells comprising the nucleic acid or the vector of the present invention into hematopoietic progenitor cells, and (2) a step of differentiating the hematopoietic progenitor cells into T cells is provided.

(1) Step of Differentiating Pluripotent Stem Cells into Hematopoietic Progenitor Cells (Step (1))

The method of differentiating pluripotent stem cells into hematopoietic progenitor cells is not particularly limited as long as it can cause differentiation into hematopoietic progenitor cells. Examples thereof include a method including culturing pluripotent stem cells in a medium for induction of hematopoietic progenitor cells, as described in, for example, WO 2013/075222, WO 2016/076415 and Liu S. et al., Cytotherapy, 17 (2015); 344-358 and the like.

In the present invention, a medium used for induction into hematopoietic progenitor cells is not particularly limited. A medium used for culturing animal cells can be prepared into a basal medium. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and a mixed medium of these. The medium may contain a serum, or may be serum-free. If necessary, the basal medium may also contain Vitamin Cs (e.g., ascorbic acid), albumin, insulin, transferrin, selenium, fatty acid, trace elements, 2-mercaptoethanol, thiol glycerol, lipids, amino acids, L-glutamine, non-essential amino acids, vitamins, growth factors, low-molecular-weight compounds, antibiotics, antioxidants, pyruvic acid, buffers, inorganic salts, cytokines, and the like.

In the present invention, the "Vitamin Cs" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. Preferred is vitamin C phosphate. Examples of the vitamin C phosphate include salts of L-ascorbic acid phosphate such as L-ascorbic acid phosphate Na and L-ascorbic acid phosphate Mg.

The basal medium to be used in step (1) is preferably IMDM medium containing serum, insulin, transferrin, selenium, thiol glycerol, L-glutamine and ascorbic acid.

The culture medium to be used in step (1) may be further supplemented with at least one kind of cytokine selected from the group consisting of BMP4 (Bone morphogenetic protein 4), VEGF (vascular endothelial growth factor), SCF (Stem cell factor), and FLT-3L (Flt3 Ligand). The medium is more preferably a culture liquid supplemented with VEGF, SCF and FLT-3L.

When Vitamin Cs is used in step (1), the Vitamin Cs is preferably added (supplied) every four days, every three days, every two days, or every day. The Vitamin Cs is preferably added every day. The addition of the Vitamin Cs to the medium is preferably carried out at an amount corresponding to 5 ng/ml to 500 ng/ml (e.g., an amount corresponding to 5 ng/ml, 10 ng/ml, 25 ng/ml, 50 ng/ml, 100 ng/ml, 200 ng/ml, 300 ng/ml, 400 ng/ml, or 500 ng/ml).

When BMP4 is used in step (1), the concentration of the BMP4 in the culture medium is not particularly limited. It is preferably 10 ng/ml-100 ng/ml (e.g., 10 ng/ml, 20 ng/ml, 30 ng/ml, 40 ng/ml, 50 ng/ml, 60 ng/ml, 70 ng/ml, 80 ng/ml, 90 ng/ml, 100 ng/ml), more preferably 20 ng/ml-40 ng/ml.

When VEGF is used in step (1), the concentration of the VEGF in the culture medium is not particularly limited. It is preferably 10 ng/ml-100 ng/ml (e.g., 10 ng/ml, 20 ng/ml, 30 ng/ml, 40 ng/ml, 50 ng/ml, 60 ng/ml, 70 ng/ml, 80 ng/ml, 90 ng/ml, 100 ng/ml), particularly preferably 20 ng/ml.

When SCF is used in step (1), the concentration of the SCF in the culture medium is not particularly limited. It is preferably 10 ng/ml-100 ng/ml (e.g., 10 ng/ml, 20 ng/ml, 30 ng/ml, 40 ng/ml, 50 ng/ml, 60 ng/ml, 70 ng/ml, 80 ng/ml, 90 ng/ml, 100 ng/ml), particularly preferably 30 ng/ml.

When FLT-3L is used in step (1), the concentration of the FLT-3L in the culture medium is not particularly limited. It is preferably 1 ng/ml-100 ng/ml (e.g., 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, 100 ng/ml), particularly preferably 10 ng/ml.

In step (1), the pluripotent stem cells may be cultured by adherent culture or suspension culture. In cases of the adherent culture, the culture may be carried out in a culture vessel coated with a coating agent, and/or may be co-cultured with other cells. Examples of the other cells for the co-culture include C3H10T1/2 (Takayama N., et al. J Exp Med. 2817-2830, 2010) and stromal cells derived from a different species (Niwa A et al. J Cell Physiol. 2009 November; 221(2): 367-77). Examples of the coating agent include Matrigel (Nivea A, et al. PLoS One. 6(7): e22261, 2011). Examples of the method of the suspension culture include the methods described in Chadwick et al. Blood 2003, 102: 906-15, Vijayaragavan et al. Cell Stem Cell 2009, 4: 248-62, and Saeki et al. Stem Cells 2009, 27: 59-67.

In step (1), the temperature conditions are not limited. The temperature is, for example, about 37° C. to about 42° C., preferably about 37 to about 39° C. The culture period may be appropriately determined by those skilled in the art by monitoring the number of hematopoietic progenitor cells and the like. The number of days of the culture is not limited as long as hematopoietic progenitor cells can be obtained. Examples of the culture period include at least 6 days, not less than 7 days, not less than 8 days, not less than 9 days, not less than 10 days, not less than 11 days, not less than 12 days, not less than 13 days, and not less than 14 days. The culture period is preferably 14 days. While a longer culture period generally does not pose a problem in the production of hematopoietic progenitor cells, it is preferably not more than 35 days, more preferably not more than 21 days. The culture may be carried out under low-oxygen conditions, and the low-oxygen condition in the present invention means, for example, oxygen concentration of 15%, 10%, 9%, 8%, 7%, 6%, 5% or lower than these.

(2) Step of Differentiating the Hematopoietic Progenitor Cells into T Cells (Step (2))

A method for differentiating the hematopoietic progenitor cells into T cells is not particularly limited as long as it can differentiate hematopoietic progenitor cells into T cells. Examples thereof include a method containing (2-1) a step of inducing CD4CD8 double positive T cells from the hematopoietic progenitor cells and (2-2) a step of inducing CD8 positive T cells from the CD4CD8 double positive T cells, as described in e.g. WO 2016/076415 and the like. It is preferable to isolate the hematopoiesis precursor in advance from the cell population obtained in step (1) by using a marker of a hematopoietic progenitor cell. As the marker, at least one selected from the group consisting of CD43, CD34, CD31 and CD144 can be mentioned.

(2-1) Step of Inducing the Hematopoietic Progenitor Cell into the CD4CD8 Double Positive T Cell (Step (2-1))

In the present invention, examples of the differentiation method into the CD4CD8 double positive T cell include a method of culturing the hematopoietic progenitor cell in an induction medium into the CD4CD8 double positive T cell.

In the present invention, a medium for inducing differentiation into the CD4CD8 double positive T cell is not particularly limited, and a medium used for culturing animal cells can be prepared into a basal medium. Examples of the basal medium include those similar to the basal medium used in the above-mentioned step (1). The medium may contain serum, or may be serum-free. If necessary, the basal medium may also contain Vitamin Cs, albumin, insulin, transferrin, selenium, fatty acid, trace elements, 2-mercaptoethanol, thiol glycerol, lipids, amino acids, L-glutamine, non-essential amino acids, vitamins, growth factors, low-molecular-weight compounds, antibiotics, antioxidants, pyruvic acid, buffers, inorganic salts, cytokines, and the like.

A preferable basal medium to be used in step (2-1) is αMEM medium containing serum, transferrin, selenium and L-glutamine. When Vitamin Cs is added to the basal medium, Vitamin Cs is the same as that in step (1).

The culture medium used in step (2-1) may further contain cytokine FLT-3L and/or IL-7, more preferred is a culture medium containing FLT-3L and IL-7.

When IL-7 is used in step (2-1), the concentration of the IL-7 in the culture medium is preferably 1 ng/ml-50 ng/ml (e.g., 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 30 ng/ml, 40 ng/ml, 50 ng/ml), particularly preferably 5 ng/ml.

When FLT-3L is used in step (2-1), FLT-3L can be used similarly to the above-mentioned step (1).

In step (2-1), the hematopoietic progenitor cells may be cultured by adherent culture or suspension culture. In cases of the adherent culture, a coated culture vessel may be used, and/or the hematopoietic progenitor cells may be co-cultured with feeder cells and the like. Examples of the feeder cell for the co-culture include a bone-marrow stromal cell line, OP9 cell (available from Riken BioResource Center). The OP9 cell is preferably OP-DL1 cell, which constantly expresses Dll1 (Holmes R I and Zuniga-Pflucker J C. Cold Spring Harb Protoc. 2009(2)). In the present invention, in cases where OP9 cells are used as the feeder cells, Dll1, or a fusion protein of Dll1 and Fc or the like, separately prepared may be added to the medium to perform the co-culture. In the present invention, examples of the Dll1 include proteins encoded by a gene having the nucleotide sequence of the NCBI accession number NM #005618 in the case of human, or NCBI accession number NM #007865 in the case of mouse; and naturally occurring mutants having a high sequence identity (for example, having a sequence identity of not less than 90%) to these proteins and having an equivalent function. In cases where feeder cells are used for production of the CD4/CD8 double-positive T cells, the feeder cells are preferably appropriately replaced during the culture. The replacement of the feeder cells may be carried out by transferring the subject cells that are being cultured onto feeder cells that are preliminarily plated. The replacement may be carried out every five days, every four days, every three days, or every two days.

In step (2-1), the culture temperature conditions are not limited. The temperature is, for example, about 37° C. to about 42° C., preferably about 37 to about 39° C. The culture period may be appropriately determined by those skilled in the art by monitoring of the number of CD4/CD8 double-positive T cells and the like. The number of days of the culture is not limited as long as hematopoietic progenitor cells can be obtained. Examples of the culture period include at least not less than 10 days, not less than 12 days, not less than 14 days, not less than 16 days, not less than 18 days, not less than 20 days, not less than 22 days, and not less than 23 days. The culture period is preferably 23 days. In addition, not more than 90 days is preferable, and not more than 42 days is more preferable.

(2-2) Step of Inducing CD8 Positive T Cells from the CD4CD8 Double Positive (DP) T Cells (Step (2-2))

The CD4/CD8 DP cells obtained by step (2-1) can be induced to differentiate into CD8 single positive (SP) cells by subjecting them to a step for inducing differentiation into CD8 single positive (SP) cells.

Examples of the basal medium and medium to be used in step (2-2) include those similar to the basal medium and medium used in step (1).

The aforementioned medium may contain an adrenocortical hormone agent. Examples of the adrenocortical hormone agent include, for example, a glucocorticoid and a derivative thereof. Examples of the glucocorticoid include, for example, cortisone acetate, hydrocortisone, fludrocortisone acetate, prednisolone, triamcinolone, methylprednisolone, dexamethasone, betamethasone, and beclometasone dipropionate. Of these, dexamethasone is preferable.

When dexamethasone is used as the adrenocortical hormone agent, the concentration of the dexamethasone in the culture medium is preferably 1 nM-100 nM (e.g., 1 nM, 5 nM, 10 nM, 20 nM, 30 nM, 40 nM, 50 nM, 60 nM, 70 nM, 80 nM, 90 nM, 100 nM), particularly preferably 10 nM.

The aforementioned medium may contain an antibody (e.g., anti-CD3 antibody, anti CD28 antibody, anti CD2 antibody), cytokine (e.g., IL-7, IL-2, IL-15) and the like.

When an anti-CD3 antibody is used in step (2-2), the anti-CD3 antibody is not particularly limited as long as it specifically recognizes CD3. For example, an antibody produced from OKT3 clone can be mentioned. The anti-CD3 antibody may be bonded to magnetic beads and the like or, instead of adding the aforementioned anti-CD3 antibody to the medium, stimulation may be given by incubating the T lymphocytes for a given period on a culture vessel to which the anti-CD3 antibody is bound on the surface thereof. The concentration of the anti-CD3 antibody in the medium is preferably 10 ng/ml-1000 ng/ml (e.g., 10 ng/ml, 50 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1000 ng/ml), particularly preferably 500 ng/ml. The concentration of other antibodies can also be appropriately determined by those of ordinary skill in the art based on the culture conditions and the like.

When IL-2 is used in step (2-2), the concentration of the IL-2 in the medium is preferably 10 U/ml-1000 U/ml (e.g., 10 U/ml, 20 U/ml, 30 U/ml, 40 U/ml, 50 U/ml, 60 U/ml, 70 U/ml, 80 U/ml, 90 U/ml, 100 U/ml, 200 U/ml, 500 U/ml, 1000 U/ml), particularly preferably 100 U/ml. The concentration of the IL-7 or IL-15 in the medium used in step (2-2) is preferably 1 ng/ml-100 ng/ml (e.g., 1 ng/ml, 5 ng/ml, 10 ng/ml, 20 ng/ml, ng/ml, 40 ng/ml, 50 ng/ml, 60 ng/ml, 70 ng/ml, 80 ng/ml, 90 ng/ml, 100 ng/ml), particularly preferably 10 ng/ml.

In step (2-2), the temperature conditions are not particularly limited. The temperature is preferably about 37° C. to about 42° C., more preferably about 37 to about 39° C. The culture period may be appropriately determined by those skilled in the art by monitoring of the number of CD8-positive T cells and the like. The number of days of the culture is not limited as long as CD8-positive T cells can be obtained. The culture period is preferably not less than 1 day, not less than 3 days, not less than 7 days, and preferably not more than 60 days, more preferably not more than 35 days.

6. Medicament Containing the Nucleic Acid, the Vector or the Cell of the Present Invention The present invention provides a medicament containing the nucleic acid, the vector or the cell of the present invention as an active ingredient (hereinafter to be abbreviated as "the medicament of the present invention"). A cell comprising the nucleic acid of the present invention may exhibit a cytotoxic activity against cells presenting HLA-A24 molecule and $GPC3_{298-306}$ peptide, or HLA-A02 molecule and $GPC3_{144-152}$ peptide. Therefore, a medicament containing the nucleic acid, the vector or the cell of the present invention can be used for the prevention or treatment of a disease expressing GPC3, and can be administered, for example, to mammals (e.g., mouse, rat, hamster, rabbit, cat, dog, bovine, sheep, monkey, human), preferably humans. While the disease expressing GPC3 is not particularly limited, for example, cancer, tumor and the like expressing GPC3 can be mentioned. Therefore, in a preferable embodiment of the present invention, an anti-cancer agent for the prevention or treatment of cancer and tumor expressing GPC3 is provided.

Such cancer and tumor expressing GPC3 are described in, for example, "Daniel Baumhoer et al., Am J. Clin Pathol, 2008, 129, 899-906" and the like. Specific examples thereof include, but are not limited to, liver cancer (e.g., hepatoma), ovarian cancer (e.g., ovary clear cell adenocarcinoma), childhood cancer, lung cancer (e.g., squamous cell carcinoma, small cell lung cancer), testis cancer (e.g., nonseminomas germ cell tumor), soft tissuetumor (e.g., liposarcoma, malignant fibrous histiocytoma), uterine cancer (e.g., cervix intraepithelial tumor, cervix squamous cell carcinoma), melanoma, adrenal gland tumor (e.g., adrenal gland adenoma), neurotic tumor (e.g., schwannoma), gastric cancer (e.g., adenocarcinoma of stomach), renal cancer (e.g., Grawitz tumor), breast cancer (e.g., invasive lobular carcinoma, mucous cancer), thyroid cancer (e.g., medullar cancer), laryngeal cancer (e.g., squamous cell carcinoma), urinary bladder cancer (e.g., invasive transitional cell carcinoma) and the like. Of these, liver cancer, ovarian cancer, childhood cancer and lung cancer are preferable, and liver cancer, particularly hepatoma, is preferable from the aspect of the expression level of GPC3.

When the nucleic acid or the vector is used as the active ingredient of the medicament of the present invention, it is preferably mixed with a known pharmaceutically acceptable carrier (excipient, diluent, filler, binder, lubricant, anticaking agent, disintegrant, surfactant and the like) and a conventionally-used additive and the like and prepared as a pharmaceutical composition. Excipients are well known to those of ordinary skill in the art and include, for example, phosphate buffered saline (e.g., 0.01 M phosphate, 0.138 M NaCl, 0.0027 M KCl, pH 7.4), aqueous solution containing mineral acid salt such as hydrochloride, hydrobromide, phosphate, sulfate and the like, physiological saline, solution of glycol or ethanol and the like, and salt of organic acid such as acetate, propionate, malonate, benzoate and the like, and the like can be mentioned. In addition, an adjuvant such as wetting agent or emulsifier and the like, and pH buffering agent can also be used. Furthermore, a preparation adjuvant such as suspending agent, preservative, stabilizer and dispersing agent and the like, and the like may also be used. Also, the above-mentioned pharmaceutical composition may be in a dry form for reconstitution with an appropriate sterile liquid prior to use. The pharmaceutical composition can be orally or parenterally administered systemically or topically according to the form to be prepared (agent for oral administration such as tablet, pill, capsule, powder, granule, syrup, emulsion, suspension and the like; agent for parenteral administration such as injection, drip infusion, external preparation, suppository and the like) and the like. For parenteral administration, intravenous administration, intradermal administration, subcutaneous administration, rectal administration, transdermal administration and the like are possible. When used in an injection form, acceptable buffering agent, solubilizing agent, isotonicity agent, and the like can also be added.

When the active ingredient is a nucleic acid, the nucleic acid is administered within the range of 0.001 mg-10 mg/kg body weight/dose. For example, for administration to a human patient, it is administered within the range of 0.001-50 mg to a patient with body weight 60 kg. When the active ingredient is a virus vector particle, it is administered within the range of about $1\times10^3$ pfu-$1\times10^{15}$ pfu in the virus titer per dose to a patient with body weight 60 kg. The above-mentioned doses are examples, and the dose can be appropriately selected according to the kind of the nucleic acid or the vector, administration route, and age, body weight, symptom and the like of the subject of administration or patient.

When the cell of the present invention is used as the active ingredient of the medicament of the present invention, the cell may be cultured and/or stimulated using an appropriate medium and/or a stimulating molecule before administration to a subject. Examples of the stimulating molecule include, but are not limited to, cytokines, suitable protein, other components and the like. Examples of the cytokines include IL-2, IL-7, IL-12, IL-15, IFN-γ and the like, and IL-2 can be preferably used. While the concentration of IL-2 in the medium is not particularly limited, for example, it is preferably 0.01-$1\times10^5$ U/mL, more preferably 1-$1\times10^4$ U/mL. Examples of the suitable protein include CD3 ligand, CD28 ligand, and anti-IL-4 antibody. Besides these, a lymphocyte stimulating factor such as lectin and the like can also be added. Furthermore, serum or plasma may be added to the medium. While the amount of addition to these media is not particularly limited, 0% by volume-20% by volume can be mentioned. In addition, the amount of the serum or plasma to be used can be changed according to the culturing stage. For example, the serum or plasma concentration can be reduced stepwise. The origin of the serum or plasma may be either self or non-self, and autologous one is preferable from the aspect of safety.

In the present invention, the medicament containing the cell of the present invention as an active ingredient is preferably used by parenteral administration to the subject. Examples of the method for parenteral administration include intravenous, intraarterial, intramuscular, intraperitoneal, and subcutaneous administration and the like. While the dose is appropriately selected according to the condition, body weight, age and the like of the subject, the medicament is generally administered such that the cell number is generally $1\times10^6$-$1\times10^{10}$ cells, preferably $1\times10^7$-$1\times10^9$ cells, more preferably $5\times10^7$-$5\times10^8$ cells, per dose to a subject with body weight 60 kg. The medicament may be administered once, or in multiple divided portions. The medicament of the present invention can be formulated into a known form suitable for parenteral administration, for example, injection or injecting agent. The medicament of the present invention may contain pharmacologically acceptable excipients as appropriate. As the pharmacologically acceptable excipient, those described above can be mentioned. The medicament of the present invention may contain saline, phosphate buffered saline (PBS), medium and the like to maintain the cells stably. The medium is not particularly limited, and examples thereof include, but are not limited to, media such as RPMI, AIM-V, X-VIVO10 and the like. The medicament may contain a pharmaceutically acceptable carrier (e.g., human serum albumin), preservative and the like for stabilizing purposes.

Furthermore, since the cell of the present invention can kill cells expressing GPC3, it can be used as a killing agent for cells expressing GPC3. Such killing agent can be prepared and used in the same manner as the aforementioned medicament.

In addition, the TCR of the present invention may also be used as a fusion protein in which, for example, the TCR is combined with a single chain antibody fragment (scFv) of an anti-CD3 antibody (or a similar antibody fragment that binds to T cells and activates T cell response). In such fusion protein, a new artificial disulfide bond may be introduced between respective constant regions of the polypeptides of two TCR chains to afford a stable, soluble high affinity TCR. The scFv of the fusion protein is preferably fused to the constant region of the β chain of the TCR. Such fusion protein is described in, for example, U.S. Pat. No. 7,569,664, Liddy et al., Nat. Med. 18:908-7 (2012), Oates and Jakobsen, OncoImmunology 2: e22891 (2013) and the like.

When such fusion protein is introduced into a living body, it binds to cells expressing GPC3 through specific recognition of the TCR, and the ScFv binds to CD3 present on the cell surface of cytotoxic T cells, whereby cells expressing GPC3 can be damaged. Therefore, a medicament containing the aforementioned fusion protein or nucleic acid encoding this protein can also be used for the prevention or treatment of a disease expressing GPC3, like a medicament containing the nucleic acid or the cell of the present invention. When used as a medicament, it can be prepared in the same manner as the aforementioned medicament.

SEQ ID NOs: in the Sequence Listing in the present specification show the following sequences.
(SEQ ID NO: 1) amino acid sequence CDR1 of TCR1-1α chain
(SEQ ID NO: 2) amino acid sequence CDR2 of TCR1-1α chain
(SEQ ID NO: 3) amino acid sequence CDR3 of TCR1-1α chain (SEQ ID NO: 4) amino acid sequence CDR1 of TCR1-2α chain
(SEQ ID NO: 5) amino acid sequence CDR2 of TCR1-2α chain
(SEQ ID NO: 6) amino acid sequence CDR3 of TCR1-2α chain
(SEQ ID NO: 7) amino acid sequence CDR1 of TCR1-1β chain
(SEQ ID NO: 8) amino acid sequence CDR2 of TCR1-1β chain
(SEQ ID NO: 9) amino acid sequence CDR3 of TCR1-1β chain
(SEQ ID NO: 10) amino acid sequence CDR1 of TCR1-2β chain
(SEQ ID NO: 11) amino acid sequence CDR2 of TCR1-2β chain
(SEQ ID NO: 12) amino acid sequence CDR3 of TCR1-2β chain
(SEQ ID NO: 13) amino acid sequence CDR1 of TCR2-1α chain
(SEQ ID NO: 14) amino acid sequence CDR2 of TCR2-1α chain
(SEQ ID NO: 15) amino acid sequence CDR3 of TCR2-1α chain
(SEQ ID NO: 16) amino acid sequence CDR1 of TCR2-1β chain
(SEQ ID NO: 17) amino acid sequence CDR2 of TCR2-1β chain
(SEQ ID NO: 18) amino acid sequence CDR3 of TCR2-1β chain
(SEQ ID NO: 19) amino acid sequence of variable region of TCR1-1α chain
(SEQ ID NO: 20) amino acid sequence of variable region of TCR1-2α chain
(SEQ ID NO: 21) amino acid sequence of variable region of TCR1-1β chain
(SEQ ID NO: 22) amino acid sequence of variable region of TCR1-2β chain
(SEQ ID NO: 23) amino acid sequence of variable region of TCR2-1α chain
(SEQ ID NO: 24) amino acid sequence of variable region of TCR2-1β chain
(SEQ ID NO: 25) amino acid sequence of constant region of TCR α chain
(SEQ ID NO: 26) amino acid sequence of constant region of TCR β chain
(SEQ ID NO: 27) amino acid sequence of $GPC3_{298\text{-}306}$ peptide
(SEQ ID NO: 28) amino acid sequence of $GPC3_{144\text{-}152}$ peptide
(SEQ ID NO: 29) full-length amino acid sequence of TCR1-1α chain
(SEQ ID NO: 30) full-length amino acid sequence of TCR1-2α chain
(SEQ ID NO: 31) full-length amino acid sequence of TCR1-1β chain
(SEQ ID NO: 32) full-length amino acid sequence of TCR1-2β chain
(SEQ ID NO: 33) full-length amino acid sequence of TCR2-1α chain
(SEQ ID NO: 34) full-length amino acid sequence of TCR2-1β chain
(SEQ ID NO: 35) forward primer for TCR1-206 chain PCR amplification
(SEQ ID NO: 36) reverse primer for TCR1-206 chain amplification
(SEQ ID NO: 37) forward primer for TCR1-2β chain PCR amplification
(SEQ ID NO: 38) reverse primer for TCR1-2β chain PCR amplification
(SEQ ID NO: 39) forward primer for TCR1-2α chain sequence
(SEQ ID NO: 40) reverse primer for TCR1-2α chain sequence
(SEQ ID NO: 41) reverse primer for TCR1-2α chain sequence
(SEQ ID NO: 42) reverse primer for TCR1-2α chain sequence
(SEQ ID NO: 43) forward primer for TCR1-2β chain sequence
(SEQ ID NO: 44) forward primer for TCR1-2β chain sequence
(SEQ ID NO: 45) reverse primer for TCR1-2β chain sequence
(SEQ ID NO: 46) reverse primer for TCR1-2β chain sequence
(SEQ ID NO: 47) full-length amino acid sequence of TCR1-1'α chain
(SEQ ID NO: 48) full-length amino acid sequence of TCR1-2'α chain
(SEQ ID NO: 49) full-length amino acid sequence of TCR1-1'β chain
(SEQ ID NO: 50) full-length amino acid sequence of TCR1-2'β chain
(SEQ ID NO: 51) full-length amino acid sequence of TCR2-1'α chain
(SEQ ID NO: 52) full-length amino acid sequence of TCR2-1'β chain
(SEQ ID NO: 53) modified amino acid sequence of constant region of TCR α chain
(SEQ ID NO: 54) modified amino acid sequence of constant region of TCR β chain
(SEQ ID NO: 55) amino acid sequence of $HIV_{19\text{-}27}$
(SEQ ID NO: 56) amino acid sequence of $HIV_{583\text{-}591}$ The present invention is explained in more detail in the following by referring to Examples, which are mere exemplifications and do not limit the present invention.

The abbreviations in the Examples follow the examples commonly used at present in the pertinent technical field, and have, for example, the following meanings.

HLA: Human Leukocyte Antigen
HIV: human immunodeficiency virus
ELISPOT: Enzyme-Linked ImmunoSpot
TAP: Transporter associated with Antigen Processing

EXAMPLES

Example 1

A vaccine obtained by mixing and emulsifying an antigen (HLA-A*24:02-restricted $GPC3_{298\text{-}306}$ peptide (hereinafter to be abbreviated as "$GPC3_{298\text{-}306}$ peptide") (SEQ ID NO: 27: EYILSLEEL; American Peptide) synthesized according to the guideline of Good Manufacturing Practice or HLA-A*02:01-restricted $GPC3_{144\text{-}152}$ peptide (hereinafter to be abbreviated as "$GPC3_{144\text{-}152}$ peptide") (SEQ ID NO: 28: FVGEFFTDV; American Peptide)) and incomplete Freund's adjuvant ((IFA); Montanide ISA-51VG; Seppic) was intradermally administered to a patient with progressive hepatocellular carcinoma, and CTL clones were established from peripheral blood mononuclear cells (PBMCs) or liver tumor biopsy tissue sample obtained after the administration.

A specific method relating to establishment of CTL clones is given below.

(1) Antigens Administration

In nonrandom, nonblinded phase 1 clinical test (test name: clinical phase I test of HLA-A24 and A2 binding glypican-3 (GPC3)-derived peptide vaccine targeting progress hepatocellular carcinoma patients, UMIN test ID: UMIN000001395) accompanying dose increment of glypican-3 (GPC3) peptide in progressive hepatocellular carcinoma (HCC) patients, a vaccine was obtained by mixing and emulsifying $GPC3_{144-152}$ peptide and incomplete Freund's adjuvant was administered (30 mg peptide/body) to HLA-A2 positive patients by intradermal injection on days 1, 15, 29. At 2 weeks after the third vaccine administration, the peripheral blood was collected and subjected to the belowmentioned PBMCs isolation.

In another clinical test (test name: clinical test for evaluation of immunological effectiveness of HLA-A24 and A2 binding glypican-3 (GPC3)-derived peptide vaccine therapy targeting progress hepatocellular carcinoma patients, UMIN test ID: UMIN000005093), a vaccine obtained by mixing and emulsifying $GPC3_{298-06}$ peptide and incomplete Freund's adjuvant was administered (3 mg peptide/body) to HLA-A24 positive patients by intradermal injection every two weeks. After the 6th vaccine administration, liver tumor biopsy was performed, and the obtained tissues were subjected to the establishment of the below-mentioned CTL clone (specifically, CTL1-1). At 2 weeks after the third vaccine administration, the peripheral blood was collected, PBMCs were isolated as mentioned below and subjected to the establishment of the CTL clone (specifically, CTL1-2).

(2) Isolation of PBMCs and Establishment of CTL Bulk

The aforementioned peripheral blood (30 mL) was centrifuged using Ficoll-Paque gradient to isolated PBMCs.

Isolated PBMCs ($2\times10^6$ cells) were cultured for 14 days in an AIM-V medium added with 10 μg/mL GPC3 peptide ($GPC3_{298-306}$ peptide or $GPC3_{144-152}$ peptide), 10% human AB serum, 50 IU/ml recombinant human interleukin-2, 10 ng/ml recombinant human interleukin-15, and CTL bulk was established.

(3) Establishment of CTL Clones

Using FACSAria cell sorter, CD8 positive and GPC3 Dextramer positive cells, or CD8 positive and CD107a positive cells were isolated from PBMCs and GPC3 peptide reactive CD8$^+$ CTL bulk obtained in the above-mentioned (2). In addition, using FACSAria cell sorter, CD8 positive and GPC3 Dextramer positive cells were isolated from the biopsy tumor tissues of the above-mentioned (1). A CD8 specific antibody used for the isolation was purchased from ProImmune, a CD107a specific antibody was purchased from BD Bioscience, and $GPC3_{298-306}$/HLA-A*24:02-Dextramer and $GPC3_{144-152}$/HLA-A*02:01 Dextramer were respectively purchased from Immudex.

Respective cells obtained by the above-mentioned isolation were seeded in a 96 well plate (1 cell/well) and stimulated for 14-21 days in an AIM-V culture medium added with 10% human AB serum, IL-2 (200 U/mL) and phytohemagglutinin-P (PHA) (5 μg/mL) and using irradiated (100 Gy) nonautologous PBMCs ($8\times10^4$ cells per well) as feeder cells, whereby CTL clones were established. In the present specification, the CTL clone established from HLA-A2 positive patients is sometimes referred to as CTL2-1, and the CTL clones established from HLA-A24 positive patients is sometimes referred to as CTL1-1 (derived from biopsy tumor tissue), CTL1-2 (derived from PBMCs).

Experimental Example 1: ELISPOT Assay

An ELISPOT assay was performed to measure antigen specific CTL reaction.

CTL2-1 ($1\times10^4$ cells per well), CTL1-1 ($1\times10^5$ cells per well) and CTL1-2 ($1\times10^5$ cells per well) were cultured at 37° C. for 20 hr in the presence of 5% $CO_2$ together with cancer cell line forcibly expressing GPC3 (SK-Hep-1/hGPC3) or Mock control cancer cell line thereof (SK-Hep-1/vec). The results thereof are shown in FIGS. 1(A) and (B).

As a result, each CTL applied to this test was clarified to have interferon-γ producing ability responsive to the cancer cell expressing GPC3.

Experimental Example 2: Peptide Titration Assay

Respective CTL clones (CTL2-1, CTL1-1 and CTL1-2) established in Example 1 and T2 target cells respectively corresponding thereto were mixed at 10:1 (effector/target (E/T)=10), and cocultured for 4 hr. As T2 target cells corresponding to CTL2-1, calcein AM-labeled T2 cells (HLA-A*02:01 positive, TAP negative) and pulsed with $GPC3_{144-152}$ peptide were used and, as T2 target cells corresponding to CTL1-1 and CTL1-2, calcein AM-labeled HLA-A*24:02 forced expression T2 cells (HLA-A*02:01/A*24:02 positive, TAP negative) and pulsed with $GPC3_{298-306}$ peptide were used. When a negative control is used, the respective cells pulsed with HIV peptide were used.

Figure 2:
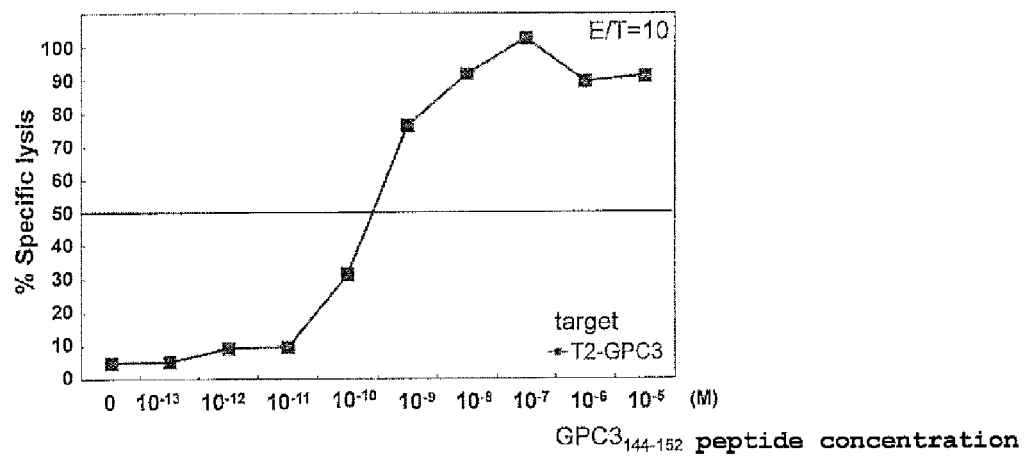
FIG. 2 shows the results of a peptide titration assay for the measurement of the recognition efficiency of the respective CTL clones against a complex of GPC3 peptide and HLA-A molecule.
Figure 2:
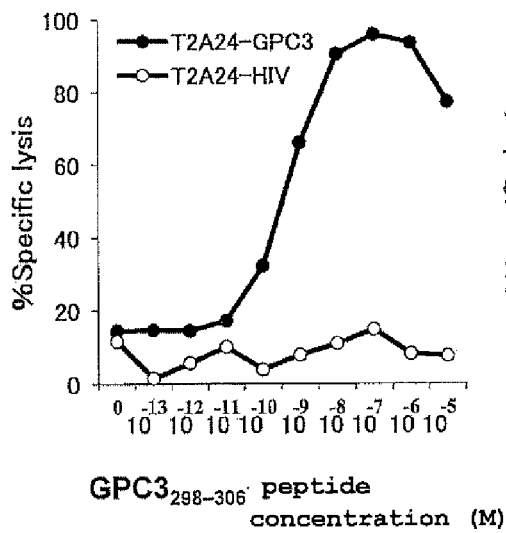
Figure 2:
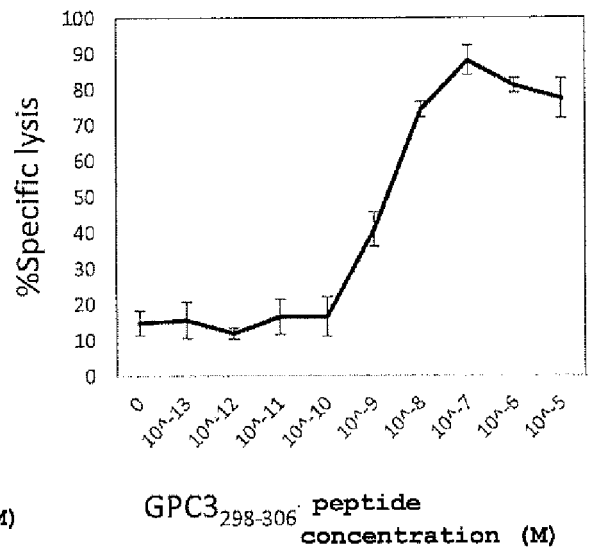

For respective CTL clones, cell toxicity rate (%) (calculated using the following calculation formula) was plotted against peptide concentration (FIGS. 2(A) and (B)).

Cell toxicity rate (%)={[(average fluorescence value of sample well−average fluorescence value of maximum free control well)/(average fluorescence value of minimum free control well−average fluorescence value of maximum free control well)]}×100

When peptide concentration at which 50% cytotoxic activity and a curve intersect is taken as the recognition efficiency of the clone, the recognition efficiency of CTL2-1 was about $10^{-10}$ M, and that of CTL1-1 was about 10-9 M.

As a result, CTL2-1 was shown to have cytotoxicity against a cell having $GPC3_{144-152}$-HLA-A*02:01 complex, and CTL1-1 and CTL1-2 were shown to have cytotoxicity against a cell having $GPC3_{298-306}$-HLA-A*24:02 complex.

Example 2: Decoding of CTL TCR Sequence

1. Sequence Decoding

Respective sequences of the TCR of CTL1-1 (i.e., TCR1-1) and the TCR of CTL2-1 (i.e., TCR2-1) were analyzed by the following method.

That is, total RNA of T cells was extracted using RNeasy Mini Kit (QIAGEN). Using Omniscript RT Kit (QIAGEN) and oligo dT primers: Invitrogen, First-Strand cDNAs were synthesized, and cDNAs were amplified by PCR. As PCR primers, a forward primer consisting of TCRAV family-specific oligonucleotide for a reconstituted T cell receptor (TCR) α chain and a reverse primer of TCRAC (Cα) constant region and a forward primer consisting of TCRBV family-specific oligonucleotide for the rearranged TCR β chain and a reverse primer of TCRBC (Cβ) constant region, which are described in Uemura Y. et al., J Immunol, 2003, 170: 947-960 or Misko et al., Proc. Natl. Acad. Sci. USA, 1999, 96: 2279-2284, were used. The amplified PCR products of the α chain and the β chain were cloned into pGEM-T plasmid vector (Promega) and the sequences were decoded. The obtained sequences were analyzed using IMGT (ImMunoGeneTics) database.

TCR of CTL1-2 (i.e., TCR1-2) sequence analysis was performed by the following method.

That is, total RNA of T cells was extracted using RNeasy Mini Kit (QIAGEN). Using SuperScriptIII reverse transcriptase (ThermoFisher Scientific) and oligodT primers (oligo dT primer: Invitrogen), First-Strand cDNA was synthesized, and cDNA was amplified by PCR. This was applied to repertoire analysis using the next generation sequencer (MiSeq, Illumina) and preliminary sequence analysis was performed. Thereafter, from the partial sequence data of repertoire analysis results, primers were designed for V region (5' untranslated region), C region (immediately before polyA addition signal of 3' untranslated region) (forward primer for TCR1-2α chain: AAGCACTCTTCTAGCCCAGAGAA (SEQ ID NO: 35), reverse primer for TCR1-2α chain: TAGCAGGGCCTCGA-TAATGA (SEQ ID NO: 36), forward primer for TCR1-2β chain: AGAATGCTTACTACAGAGACACCA (SEQ ID NO: 37), reverse primer for TCR1-2β chain: GTTTAGCC-TATTTCGTACTTGG (SEQ ID NO: 38)), and amplified by PCR. After column purification, the PCR amplification fragments were reacted using the following sequencing primers and BigDye Terminator V3.1 Cycle Sequencing Kit (ThermoFisher Scientific). The sequencing primers used were as follows;

```
forward primer for TCR1-2α chain:
                              (SEQ ID NO: 39)
ACGCCTTCAACAACAGCATTA, reverse primer for TCR1-2α chain:
                              (SEQ ID NO: 40)
CAGACTTGTCACTGGATTTAGAG, (SEQ ID NO: 41)
GGAGCACAGGCTGTCTTACAA (SEQ ID NO: 42)
ATAGCAGGGCCTCGATAATGA, forward primer for TCR1-2β chain:
                              (SEQ ID NO: 43)
AGAATGCTTACTACAGAGACACCA, (SEQ ID NO: 44)
GCTGTGTTTGAGCCATCAGAA, reverse primer for TCR1-β chain:
                              (SEQ ID NO: 45)
AGGCAGTATCTGGAGTCATTGAG, (SEQ ID NO: 46)
GTTTAGCCTATTTCGTACTTGG.
```

After column purification, sequencing was performed by ABI capillary sequencer.

Experimental Example 3: Dextramer Staining Using PBMC Introduced with TCR and Flow Cytometry Analysis 1. Construction of TCR Expression Retrovirus Vector Based on the gene sequences of TCR β chains and the gene sequences of TCR α chains identified by the above-mentioned method, an amino acid sequence incorporating cysteine substitution (specifically, 48th threonine in the constant region of the TCR α chain was substituted with cysteine, and 57th serine in the constant region of the TCR β chain of the CTL clone was substituted with cysteine) (specifically, TCR1-1'α chain designed from SEQ ID NO: 47:TCR1-1a chain, TCR1-1' β chain designed from SEQ ID NO: 48:TCR1-1β chain, TCR1-2' α chain designed from SEQ ID NO: 49:TCR1-2α chain, TCR1-2' β chain designed from SEQ ID NO: 50:TCR1-2β chain, TCR2-1' α chain designed from SEQ ID NO: 51:TCR2-1α chain, TCR2-1' β chain designed from SEQ ID NO: 52:TCR2-1β chain) was designed. Base sequences encoding amino acids of the α chains and the β chains of TCR1-1' and TCR2-1' were designed, oligo DNAs in which the designed base sequences were linked with bicistronic expression sequence T2A were artificially synthesized (GenScript) and inserted into the multi cloning site (Bgl II-Hpa I site) of retrovirus vector plasmid pDON-AI-2 (Takara Bio Inc.).

2. TCR Transgene

The virus vector plasmids obtained in the above-mentioned 1. were introduced into G3T-hi cells (Takara Bio Inc.) to obtain transient retroviral vectors. These were introduced into PG13 cells to obtain retrovirus vector-producing cells.

PBMCs isolated from healthy donors positive for HLA-A*24:02 or HLA-A*02:01 by a method similar to Example 1(2) were stimulated and incubated in 5% human plasma X-VIVO20 using an anti-CD3 antibody (clone HIT3a). Three days later, using a 24 well plate coated with RetroNectin (Takara Bio Inc.), a GPC3 ($GPC3_{298-306}$ peptide or $GPC3_{144-152}$ peptide) specific TCR (specifically, TCR1-1' or TCR2-1') was transduced using a retrovirus vector obtained from the above-mentioned retrovirus vector producing cells and transduced again the next day.

3. Dextramer Staining and Flow Cytometry Analysis

Figure 3:
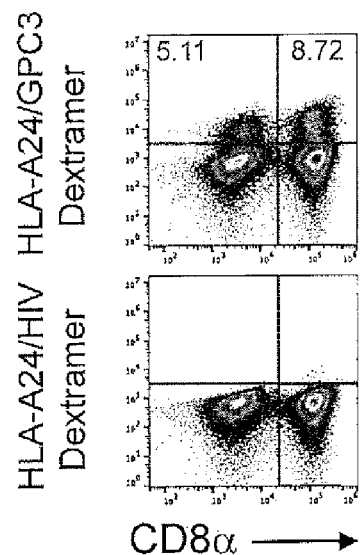
FIG. 3 shows the results of a Dextramer staining and a flow cytometry of the transformed PBMCs transfected with the TCR of the present invention.
Figure 3:
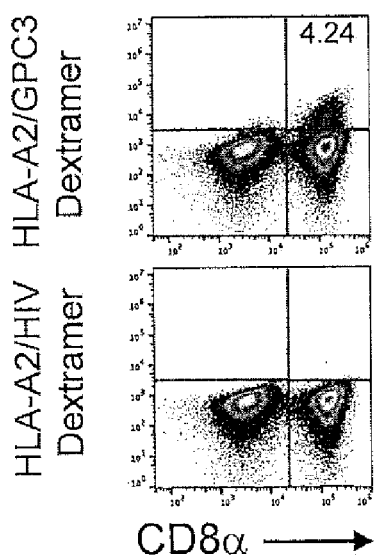

The transformed PBMCs produced in 2. were stained with HLA-A*02:01 Dextramer RPE ($GPC3_{144-152}$ (FVGEF-FTDV (SEQ ID NO: 28)), $HIV_{19-27}$ (TLNAWVKVV (SEQ ID NO: 55)); Imdex) or HLA-A*24:02 Dextramer RPE ($GPC3_{298-306}$ (EYILSLEEL (SEQ ID NO: 27)), $HIV_{583-591}$ (RYLKDQQLL (SEQ ID NO: 56)); Imdex) at room temperature for 30 min and then stained together with an anti-CD8-FITC (ProImmune) at 4° C. for 20 min. Flow cytometry was performed as described in a previous report (Ueda N and Zhang R, et al., Cellular & Molecular Immunol. 13: 1-12, 2016) and using FACSAccuri flow cytometer (BD Bioscience). The study results relating to TCR1-1' are shown in FIG. 3A, and the study results relating to TCR2-1' are shown in FIG. 3B.

In this result, a dextranomer-positive cell population was found in the CD8 positive cell population. Thus, it was revealed that functional TCR was efficiently expressed on the cell surface in PBMC in which each TCR was introduced.

Example 3

Production of expression vectors incorporating genes encoding TCRs of the present invention, production of T cell-derived iPS cell expressing the above-mentioned TCR1.

1. Production of Expression Vector Incorporating Gene Encoding TCR of the Present Invention 1) Production of Lentivirus Vector Incorporating TCR1-1'

Using CS-UbC-RfA-IRES2-hKO1 vector provided by Dr. Miyoshi Hiroyuki of Institute of Physical and Chemical Research, LR Clonase (Life Technologies) reaction with Gateway Entry vector incorporating TCR1-1' was performed to produce CS-UbC-RfA-IRES2-hKO1/TCR1-1' plasmid introduced with TCR1-2'.

2) Production of Lentivirus Supernatant Incorporating TCR1-1'

CS-UbC-RfA-IRES2-hKO1/TCR1-1' was introduced into a packaging cell LentiX-293T and the culture supernatant containing the lentivirus was recovered. The virus was concentrated by ultracentrifugation.

3) Establishment of TCR1-1' Transduced-iPS Cell iPS cells (Ff-101s04 strain) cultured on iMatrix (Nippi) were infected with CS-UbC-RfA-IRES2-hKO1/TCR1-1' virus fluid.

4) Differentiation of TCR1-2'/iPS Cells into T Cells

On day 4 of infection, infected iPS cells were detached from the dish, and hKO1 expressing cells were sorted using FACS Aria III without staining (in the present specification, cells after sorting are sometimes referred to as TCR1-1' transgene Ff-101s04). The cells sorted on hKO1 positive were differentiated in T cell direction according to the method described in WO 2017/221975, and expression of various markers in the cells after differentiation was studied using FACS Aria III.

Figure 4:
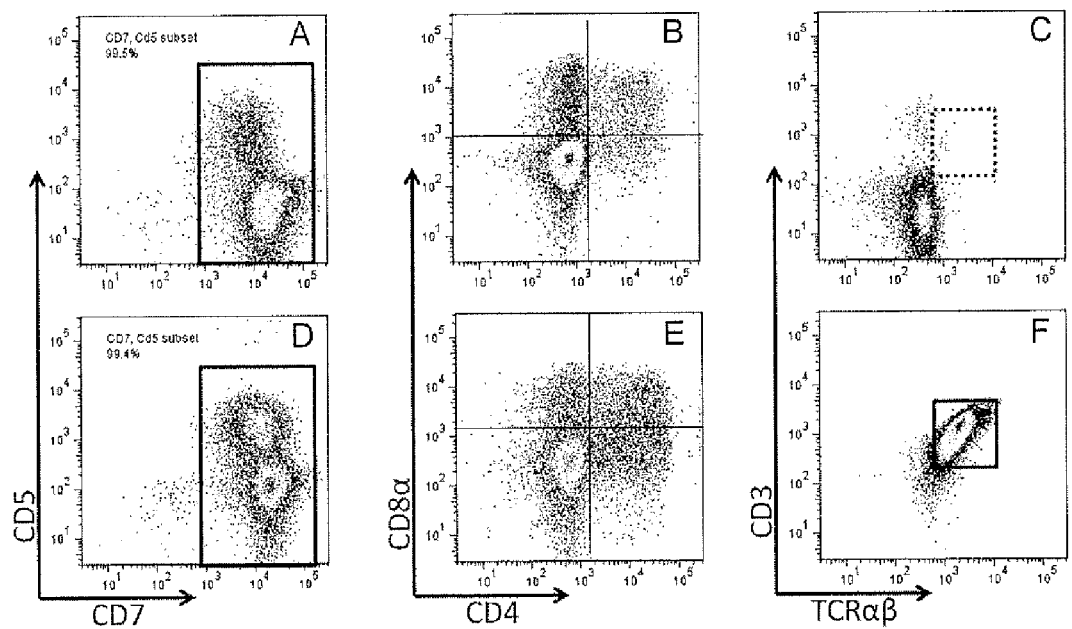
FIG. 4 shows expression of T cell markers in the differentiated T cells derived from Ff-I01s04 cells introduced with TCR1-1' gene, or Ff-I01s04 cells without the gene transfection. In the Figure, the upper panels (A, B and C) show expression of T cell markers in the differentiated T cells derived from Ff-I01s04 cell without the gene transfection, and the lower panels (D, E and F) show expression of T cell markers in the differentiated T cells derived from Ff-I01s04 cells introduced with the gene, or Ff-I01s04 cells without the gene transfection.

The results of the above-mentioned investigation are shown in FIG. 4. As shown in the lower panel of FIG. 4, it was clarified that T cells expressing a complex of TCR1-1' α chain and TCR1-1' β chain on the cellular membrane surface can be induced by subjecting TCR1-1' transgene Ff-101s04 cells to the above-mentioned differentiation operation.

Experimental Example 4

Cytotoxicity Test of iPS Cell-Derived T Cells Expressing the TCR of the Present Invention The cytotoxicity of T cells derived from iPS cells expressing TCR1-1' was measured by chrome release assay. To be specific, to HLA-*24:02 positive or HLA-A*24:02 negative lymphoblastoid cell lines (LCL) added with or not added with GPC3 antigen peptide was added aqueous $Na_2{}^{51}CrO_4$ solution (3.7 MBq) to label same at 37° C. for 1 hr and the cell lines were used as the target cells. Effector cells were added to the target cells at a ratio shown in FIG. 5, and the mixture was reacted at 37° C. for 4 hr. The cytotoxic activity (% lysis) was calculated according to the following formula based on the amount of $^{51}Cr$ liberated in the supernatant after the reaction.

% lysis=(measurement value−average minimum release value)/(average maximum release value/average minimum release value)×100

In the above formula, the minimum release value is the amount of $^{51}Cr$ released in the well not added with the effector cells and shows a spontaneous release amount of $^{51}Cr$ from the target cells. The maximum release value shows a release amount of $^{51}Cr$ when the target cells were degraded by adding 1% Triton X-100.

Figure 5:
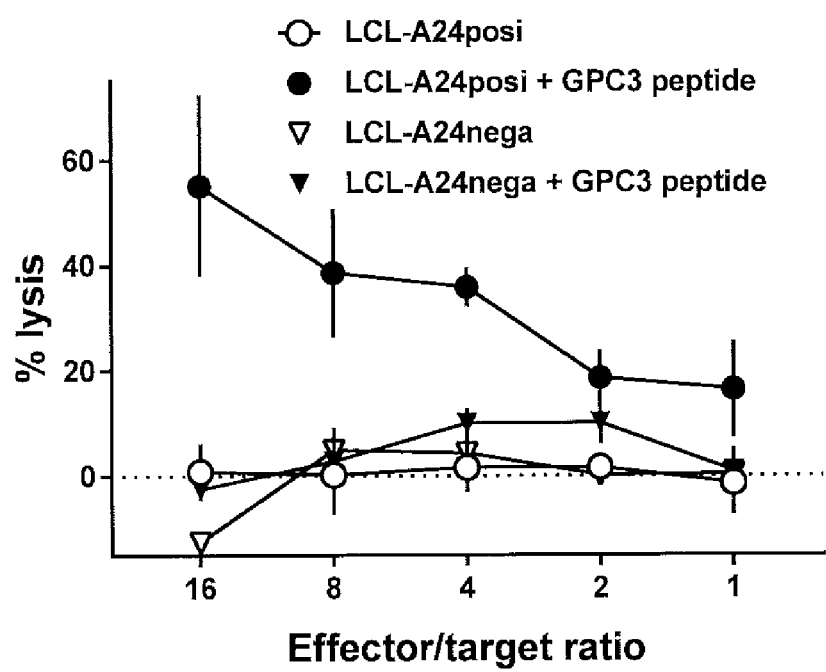
FIG. 5 shows the results of a cytotoxic activity test of the iPS cell-derived T cells expressing TCR1-1', which were added or not added with GPC3 antigen peptide, against HLA-A24 positive or HLA-A24 negative lymphoblastoid cell line (LCL).

The results of the test are shown in FIG. 5. From FIG. 5, it was shown that T cells derived from iPS cells expressing TCR1-1' exhibits cytotoxic activity only against HLA-A24 positive LCL added with GPC3 peptide.

Experimental Example 5

Cytotoxicity Test (2) of iPS Cell-Derived T Cells Expressing the TCR of the Present Invention The cytotoxicity of the T cell derived from iPS cell expressing TCR1-1' was measured by CyteCell Imaging System. To be specific, to the target cells (JHH7 strain, HepG2 strain or SK-Hep-1 strain (all human liver cancer cell lines)) were added Calcein-AM (Dojindo) solution to label same at 37° C. for 30 min. Then, Hoechst33342 (ThermoFisher) solution was added to label same at 37° C. for 20 min. Effector cells were added to the target cells at a ratio shown in FIG. 5, and the mixture was reacted at 37° C. for 4 hr. Green fluorescence positive and blue fluorescence positive cells were counted as the surviving cells (viable target cell count (VTCC)), and the cytotoxic activity (% lysis) of the above-mentioned T cells was calculated according to the following formula.

% lysis=1−[(average VTCC measured actually−average maximum release VTCC)/(average VTCC in well free of effector cells−average maximum release VTCC)]×100

In the above formula, the maximum release VTCC shows VTCC when the target cells were degraded by adding 1% Triton X-100.

Figure 6:
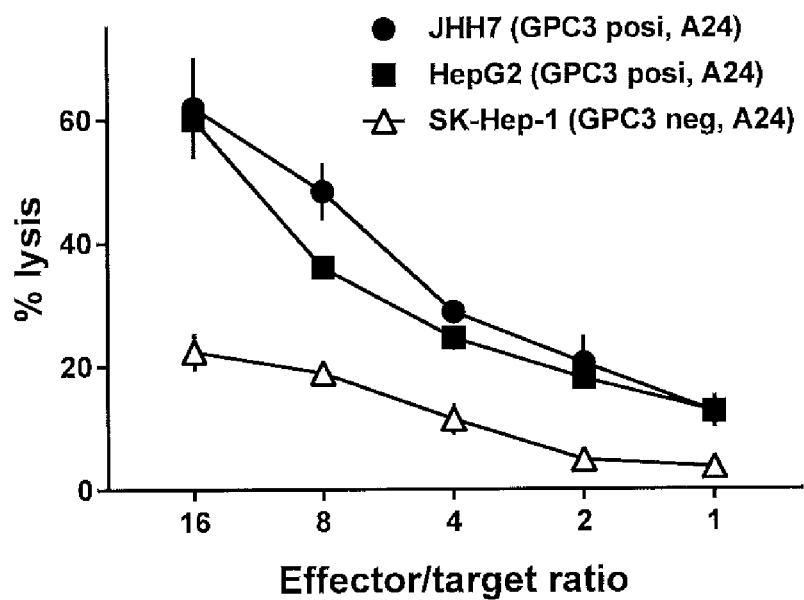
FIG. 6 shows the results of a cytotoxic activity test of the iPS cell-derived T cells expressing TCR1-1' against GPC3 positive, HLA-A*24:01 positive human liver cancer cell line.

The results of the test are shown in FIG. 6. From FIG. 6, it was shown that T cells derived from iPS cells expressing TCR1-1' has cytotoxicity against HLA-A24 positive and GPC3 positive liver cancer cells (JHH7 strain and HepG2 strain).

INDUSTRIAL APPLICABILITY

According to the present invention, a T cell receptor having binding ability to GPC3 peptide (HLA-A24-restricted $GPC3_{298-306}$ peptide and HLA-A02-restricted $GPC3_{144-152}$ peptide) or a complex of the peptide and HLA-A molecule (HLA-A24 or HLA-A02) and a nucleic acid encoding them are provided. A nucleic acid encoding the aforementioned T cell receptor can impart cytotoxic activity against a cell presenting HLA-A molecule and GPC3 peptide to T cells, and therefore, it is useful for the prevention or treatment of a disease expressing GPC3.

This application is based on a patent application No. 2017-019883 filed in Japan (filing date: Feb. 6, 2017), the contents of which are incorporated in full herein.

The invention claimed is:

1. A T cell receptor (TCR) comprising, as complementarity determining regions of the α chain,
the amino acid sequence shown in SEQ ID NO: 1,
the amino acid sequence shown in SEQ ID NO: 2, and
the amino acid sequence shown in SEQ ID NO: 3; or
the amino acid sequence shown in SEQ ID NO: 4,
the amino acid sequence shown in SEQ ID NO: 5, and
the amino acid sequence shown in SEQ ID NO: 6, and as complementarity determining regions of the β chain,
the amino acid sequence shown in SEQ ID NO: 7,
the amino acid sequence shown in SEQ ID NO: 8, and
the amino acid sequence shown in SEQ ID NO: 9; or
the amino acid sequence shown in SEQ ID NO: 10,
the amino acid sequence shown in SEQ ID NO: 11, and
the amino acid sequence shown in SEQ ID NO: 12.

2. The T cell receptor (TCR) according to claim 1 comprising, as an α chain variable region,
the amino acid sequence shown in SEQ ID NO: 19,
the amino acid sequence shown in SEQ ID NO: 19 wherein one or several amino acids are deleted, substituted or added, or
an amino acid sequence having 90% or more identity with the amino acid sequence shown in SEQ ID NO: 19; or
the amino acid sequence shown in SEQ ID NO: 20,
the amino acid sequence shown in SEQ ID NO: 20 wherein one or several amino acids are deleted, substituted or added, or
an amino acid sequence having 90% or more identity with the amino acid sequence shown in SEQ ID NO: 20, and as a β chain variable region,
the amino acid sequence shown in SEQ ID NO: 21,
the amino acid sequence shown in SEQ ID NO: 21 wherein one or several amino acids are deleted, substituted or added, or
an amino acid sequence having 90% or more identity with the amino acid sequence shown in SEQ ID NO: 21; or
the amino acid sequence shown in SEQ ID NO: 22,
the amino acid sequence shown in SEQ ID NO: 22 wherein one or several amino acids are deleted, substituted or added, or
an amino acid sequence having 90% or more identity with the amino acid sequence shown in SEQ ID NO: 22.

3. The T cell receptor according to claim 1, comprising as an α chain constant region,
the amino acid sequence shown in SEQ ID NO: 25,
the amino acid sequence shown in SEQ ID NO: 25 wherein one or several amino acids are deleted, substituted or added, or
an amino acid sequence having 90% or more identity with the amino acid sequence shown in SEQ ID NO: 25, and as a β chain constant region,
the amino acid sequence shown in SEQ ID NO: 26,
the amino acid sequence shown in SEQ ID NO: 26 wherein one or several amino acids are deleted, substituted or added, or
an amino acid sequence having 90% or more identity with the amino acid sequence shown in SEQ ID NO: 26.

4. A nucleic acid encoding the T cell receptor according to claim 1.

5. An expression vector comprising the nucleic acid according to claim 4.

6. An isolated cell comprising the nucleic acid according to claim 4.

7. The isolated cell according to claim 6, wherein said cell is a lymphocyte or a pluripotent stem cell.

8. The isolated cell according to claim 6, wherein said cell is a cytotoxic T lymphocyte.

9. A method of producing an isolated cell comprising the nucleic acid according to claim 4, comprising a step of introducing the nucleic acid into the cell.

10. A T cell induced from a pluripotent stem cell comprising the nucleic acid according to claim 4.

11. A method of producing a T cell, comprising the following steps:
   (1) a step of differentiating a pluripotent stem cell comprising the nucleic acid according to claim 4 into a hematopoietic progenitor cell, and
   (2) a step of differentiating the hematopoietic progenitor cell into a T cell.

12. The method according to claim 11, wherein said T cell is a cytotoxic T cell, in particular a CD8 positive cytotoxic T cell.

13. A medicament comprising an isolated cell,
   wherein the isolated cell comprises a nucleic acid encoding the T cell receptor, wherein the T cell receptor comprises,
   as complementarity determining regions of the α chain,
      the amino acid sequence shown in SEQ ID NO: 1,
      the amino acid sequence shown in SEQ ID NO: 2, and
      the amino acid sequence shown in SEQ ID NO: 3; or
      the amino acid sequence shown in SEQ ID NO: 4,
      the amino acid sequence shown in SEQ ID NO: 5, and
      the amino acid sequence shown in SEQ ID NO: 6, and
   as complementarity determining regions of the β chain,
      the amino acid sequence shown in SEQ ID NO: 7,
      the amino acid sequence shown in SEQ ID NO: 8, and
      the amino acid sequence shown in SEQ ID NO: 9: or
      the amino acid sequence shown in SEQ ID NO: 10,
      the amino acid sequence shown in SEQ ID NO: 11, and
      the amino acid sequence shown in SEQ ID NO: 12.

14. A method of treating cancer, comprising administering to a subject the medicament according to claim 13 in which the isolated cell is a lymphocyte or a T cell induced from a pluripotent stem cell comprising a nucleic acid encoding the T cell receptor, wherein the cancerous cells express glypican-3.

15. A method for killing a cell expressing glypican-3, comprising administering the isolated cell according to claim 6 to the cell expressing glypican-3, wherein the isolated cell is a lymphocyte or a T cell induced from a pluripotent stem cell.

16. A method of treating cancer, comprising administering to a subject an isolated cell comprising a nucleic acid encoding the T cell receptor according to claim 1, wherein the cancerous cells express glypican-3, and the isolated cell is a lymphocyte or a T cell induced from a pluripotent stem cell.

17. A method of making a therapeutic agent for treating a disease expressing glypican-3, comprising inducing a T cell from a pluripotent stem cell comprising a nucleic acid encoding the T cell receptor of claim 1.

* * * * *